US006643351B2

(12) United States Patent
Morita et al.

(10) Patent No.: US 6,643,351 B2
(45) Date of Patent: Nov. 4, 2003

(54) RADIOGRAPHIC APPARATUS

(75) Inventors: Eiichi Morita, Kyoto (JP); Yoshihiro Ueno, Kyoto (JP)

(73) Assignee: Shimadzu Corporation, Kyoto (JP)

(*) Notice: Subject to any disclaimer, the term of this patent is extended or adjusted under 35 U.S.C. 154(b) by 108 days.

(21) Appl. No.: 10/068,846

(22) Filed: Feb. 11, 2002

(65) Prior Publication Data

US 2002/0154728 A1 Oct. 24, 2002

(30) Foreign Application Priority Data

Mar. 12, 2001 (JP) ............................ 2001-068200
Mar. 13, 2001 (JP) ............................ 2001-070719

(51) Int. Cl.[7] .............................................. A61B 6/03
(52) U.S. Cl. .................................... 378/4; 378/901
(58) Field of Search .................... 378/4, 8, 15, 62, 378/901

(56) References Cited

U.S. PATENT DOCUMENTS 6,463,116 B1 * 10/2002 Oikawa .......................... 378/4
6,587,539 B2 * 7/2003 Oikawa ........................ 378/19

* cited by examiner

Primary Examiner—David V. Bruce
(74) Attorney, Agent, or Firm—Rader, Fishman & Grauer PLLC

(57) ABSTRACT

A driver drives an X-ray tube and a flat panel X-ray detector synchronously to scan sectional planes to be imaged of an object under examination. A back projection unit projects projection data detected in varied scan positions to predetermined lattice points of a three-dimensional lattice virtually set to the region of interest of the object radiographed. An image reconstruction is carried out to generate three-dimensional volume data of the region of interest. The three-dimensional volume data of the region of interest is generated quickly without repeating a radiographic operation.

20 Claims, 15 Drawing Sheets

RADIOGRAPHIC APPARATUS

BACKGROUND OF THE INVENTION

(1) Field of the Invention

This invention relates to radiographic apparatus of the non-CT (Computed Tomography) type used in medical, industrial and other fields for producing sectional images of patients or objects under examination. More particularly, the invention relates to a technique for generating a three-dimensional sectional image of a region of interest of an object quickly.

(2) Description of the Related Art

Conventional radiographic apparatus include an X-ray radiographic apparatus, for example. The X-ray radiographic apparatus has an X-ray tube and an image intensifier opposed to each other across an object under examination. The X-ray tube is linearly moved in a first direction, and in synchronism therewith the image intensifier is moved in a second direction counter to the first direction. With this movement, the apparatus intermittently performs radiography while varying an angle of X-ray emission from the X-ray tube to the object, such that a given point in a particular sectional plane of the object always corresponds to the same location on the detecting plane of the image intensifier. Then, a process is carried out simply to add detection signals so as to overlap a plurality of projected images acquired by radiography done from varied angles. In this way, the apparatus derives image information on a particular section of the object and image information on adjacent sections at opposite sides of the particular section.

Thus, the above X-ray radiographic apparatus is based on the non-CT type radiographic technique distinct from the X-ray CT type radiographic technique which has made remarkable progress in recent years. That is, the X-ray CT type radiographic technique acquires transmitted images by driving an X-ray tube and an image intensifier opposed to each other across an object under examination to make one revolution (at least a half revolution) about the body axis of the object. An image reconstruction is carried out based on transmitted images acquired while one revolution (at least a half revolution) about the body axis of the object, to produce a sectional image seen in a direction along the body axis of the object. The non-CT type radiographic technique, as does the foregoing X-ray radiographic apparatus, produces a sectional image seen in a direction along the body axis of the object, without causing the X-ray tube and image intensifier to make a half or more revolution about the body axis of the object.

However, the conventional technique noted above has the following drawback. The non-CT type radiographic apparatus cannot generate a three-dimensional sectional image of a region of interest of an object quickly.

Specifically, the conventional non-CT type radiographic apparatus can acquire, in one radiographic operation, only two-dimensional sectional images of a region of interest of an object, including only information on a particular sectional plane and adjacent sectional planes at opposite sides of the particular sectional plane in the region of interest. When it is desired to generate three-dimensional volume data (i.e. a three-dimensional sectional image) of the region of interest, the radiographic operation must be repeated a plurality of times to generate a three-dimensional sectional image by combining two-dimensional sectional images acquired by the repeated radiographic operation. This results not only in the object being exposed an increased number of times, and thus an increased burden, but the generation of a three-dimensional volume data being an extremely time-consuming process.

When, for example, it is desired to obtain a slant sectional image of a region of interest not parallel to the detecting plane of the image intensifier, the radiographic operation must, again, be repeated a plurality of times to generate a three-dimensional sectional image by combining two-dimensional sectional images acquired by the repeated radiographic operation. A desired slant image is computed from the three-dimensional sectional image. Thus, the above drawbacks arise here also.

SUMMARY OF THE INVENTION

This invention has been made having regard to the state of the art noted above, and its object is to provide a radiographic apparatus capable of generating a three-dimensional sectional image of a region of interest of an object quickly.

The above object is fulfilled, according to this invention, by a radiographic apparatus for obtaining images of sectional planes in a region of interest of an object under examination by an image reconstruction using projection data acquired by radiographing the object from varied scan positions, the apparatus comprising:

a radiation source for irradiating the object with penetrating electromagnetic waves;

an area detector opposed to the radiation source across the object for detecting electromagnetic waves transmitted through the object;

a scanning device for synchronously moving the radiation source and the area detector for scanning action; and a back projection unit for performing an image reconstruction to generate three-dimensional volume data of the region of interest by projecting projection data detected in the varied scan positions back to predetermined lattice points of a three-dimensional lattice virtually set to the region of interest of the object radiographed.

With the apparatus according to this invention, the back projection unit performs an image reconstruction to generate three-dimensional volume data of the region of interest by projecting projection data detected in the varied scan positions back to predetermined lattice points of a three-dimensional lattice virtually set to the region of interest of the object radiographed. The apparatus does not use the conventional method in which two-dimensional sectional image data is generated by adding detection signals to superimpose, on a single plane, a plurality of projection images acquired by radiography from varied angles (i.e. projection images acquired from varied scan positions). Instead, an image reconstruction is carried out to generate three-dimensional volume data of the region of interest by projecting projection images acquired from varied scan positions back to predetermined lattice points of the three-dimensional lattice. Three-dimensional volume data of the region of interest may be generated without performing radiography a plurality of times. Thus, three-dimensional volume data of the region of interest of the object is generated quickly.

Preferably, the apparatus further comprises a filtering unit for performing an |ω| filtering process on the projection data detected in the varied scan positions, and outputting the projection data to the back projection unit. This filter application effectively reduces artifacts caused by DC components being emphasized in three-dimensional volume data subsequently generated by the back projection unit.

Preferably, the area detector is a flat panel detector or an image intensifier, which enables a prompt generation of a three-dimensional image of the region of interest of the object.

Preferably, one of the radiation source and the area detector is movable linearly in a first direction, and the other movable linearly in synchronism therewith in a second direction parallel and counter to the first direction. Thus, radiography is carried out for an image reconstruction to generate three-dimensional volume data of the region of interest of the object by moving the radiation source and area detector linearly and parallel to each other with the object in between.

Preferably, the radiation source is revolved in one of parallel planes opposed to each other across the object, and the area detector is revolved in synchronism therewith in the other parallel plane in a direction counter to a direction of revolution of the radiation source. Thus, radiography is carried out for an image reconstruction to generate three-dimensional volume data of the region of interest of the object by individually revolving the radiation source and area detector in the parallel planes with the object in between.

It is also preferred that two arcuate tracks are set on a circumferential track around the object to be opposed to each other across the object, the radiation source is moved along one of the arcuate tracks, and the area detector in synchronism therewith along the other arcuate track to maintain a fixed distance from the radiation source. Thus, radiography is carried out for an image reconstruction to generate three-dimensional volume data of the region of interest of the object by individually moving the radiation source and area detector along the arcuate tracks opposed to each other across the object.

In another aspect of the invention, a radiographic apparatus is provided for obtaining images of sectional planes in a region of interest of an object under examination by an image reconstruction using projection data acquired by radiographing the object from varied scan positions, the apparatus comprising:
  a radiation source for irradiating the object with penetrating electromagnetic waves in form of a divergent beam;
  an area detector opposed to the radiation source across the object for detecting electromagnetic waves transmitted through the object;
  a scanning device for setting two non-orbital tracks opposed to each other across the object, moving the radiation source along one of the non-orbital tracks, and moving the area detector in synchronism therewith along the other non-orbital track;
  a convolution unit for performing a convolution process on the projection data detected in the varied scan positions; and
  a back projection unit for performing the image reconstruction to generate three-dimensional volume data of the region of interest by projecting the projection data convoluted by the convolution unit back to predetermined lattice points of a three-dimensional lattice virtually set to the region of interest of the object radiographed.

With this apparatus, the convolution unit performs a convolution process on the projection data detected in the varied scan positions, and the back projection unit performs an image reconstruction to generate three-dimensional volume data of the region of interest by projecting the projection data convoluted by the convolution unit back to predetermined lattice points of a three-dimensional lattice virtually set to the region of interest of the object radiographed. The apparatus does not use the conventional method in which two-dimensional sectional image data is generated by adding detection signals to superimpose, on a single plane, a plurality of projection images acquired by radiography from varied angles (i.e. projection images acquired from varied scan positions). Instead, an image reconstruction is carried out to generate three-dimensional volume data of the region of interest by projecting projection images acquired from varied scan positions back to predetermined lattice points of the three-dimensional lattice. Three-dimensional volume data of the region of interest may be generated without performing radiography a plurality of times. Thus, three-dimensional volume data of the region of interest of the object is generated quickly.

Preferably, the scanning device is arranged to move one of the radiation source and the area detector linearly in a first direction, and to move the other linearly in synchronism therewith in a second direction parallel and counter to the first direction, with the sectional planes to be imaged of the object placed in between. The back projection unit is arranged to project the projection data for the varied scan positions back to the predetermined lattice points of the three-dimensional lattice, coordinates of the projection data being corrected according to an angle formed between a virtual center axis of revolution extending substantially through the center of the region of interest of the object and perpendicular to the sectional planes to be imaged, and a straight line extending from the radiation source in each of the varied scan positions to the center of the area detector. Thus, even where the radiation source and area detector are moved linearly and in parallel to each other for scanning action, an image construction may be carried out directly on the projection data (original image data) with no need to modify, e.g. plane-shift, the projection data (original image data).

Preferably, the area detector is a flat panel detector or an image intensifier, which enables a prompt generation of a three-dimensional image of the region of interest of the object.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

<First Embodiment>

Figure 1:
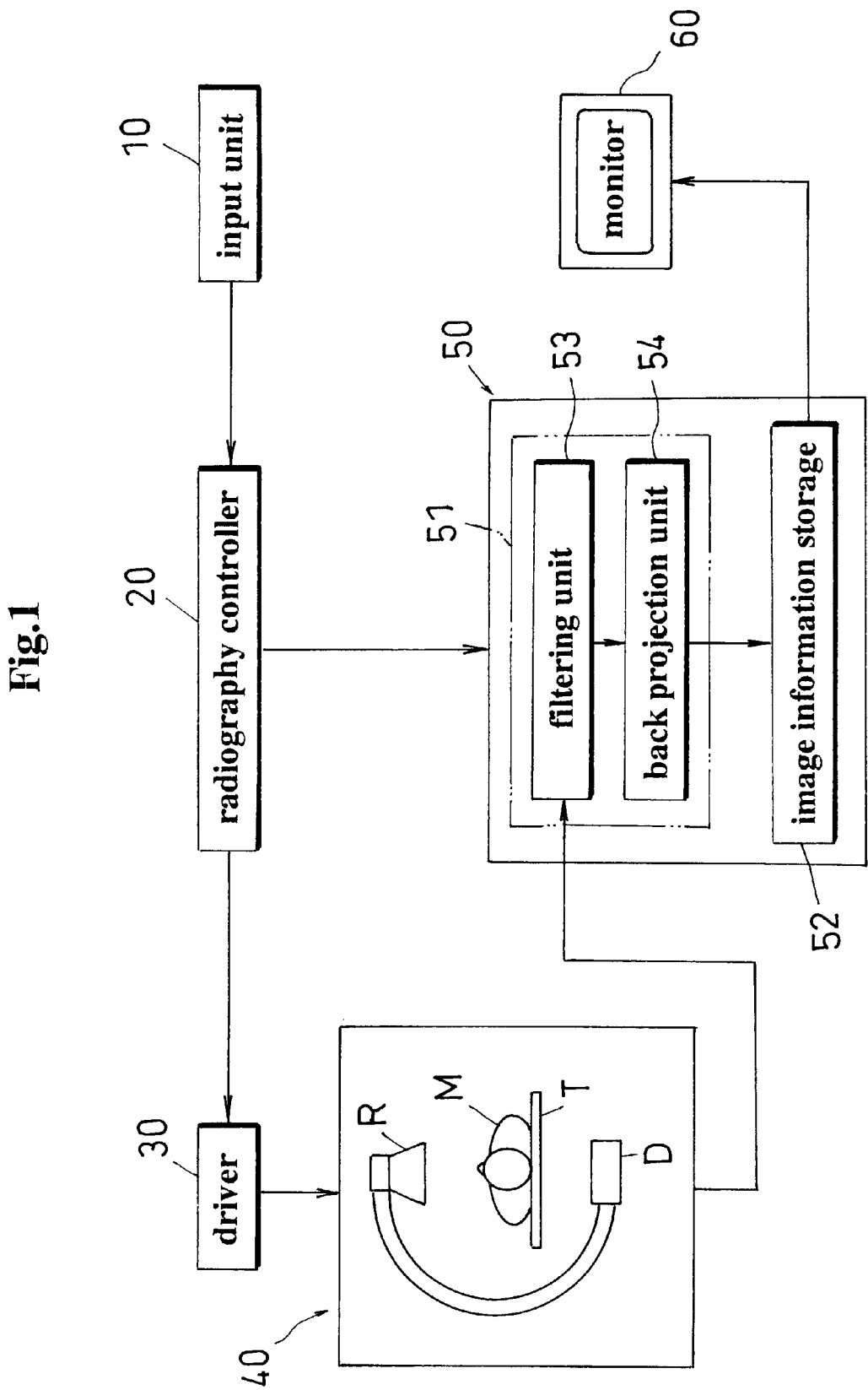
FIG. 1 is a block diagram of an X-ray radiographic apparatus in a first embodiment.

FIG. 1 is a block diagram of a non-CT type X-ray radio-graphic apparatus in a first embodiment, which is one example of radiographic apparatus according to this invention.

This X-ray radiographic apparatus includes an input unit 10 for inputting various information and instructions, a radiography controller 20 for controlling X-ray radiography based on the information and instructions inputted, a driver 30 for operating an image acquire station 40 under control of the radiography controller 20, the image acquire station 40 for picking up images of a region of interest of a patient M, a data processor 50 for performing an image reconstruction to generate three-dimensional volume data of the region of interest of patient M from image information provided by the image acquire station 40, and storing the three-dimensional volume data generated, and a monitor 60 for displaying image information stored in the data processor 50.

The construction and function of each of these components will be described hereinafter.

Figure 2:
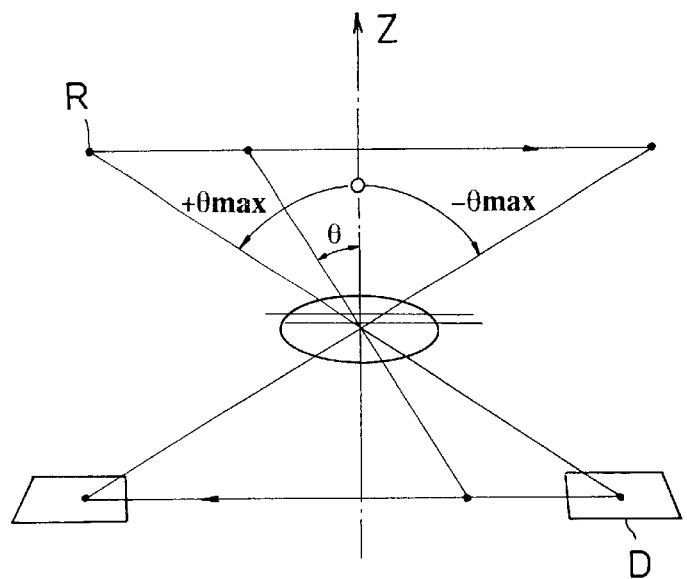
FIG. 2 is a schematic view showing an image pickup mode of the X-ray radiographic apparatus.

As shown in FIG. 2, an X-ray tube R and a flat panel X-ray detector D are opposed to each other across the patient M. The X-ray tube R is movable linearly in a first direction, and in synchronism therewith the flat panel X-ray detector D is movable linearly in a second direction parallel and counter to the first direction. Radiography is performed intermittently while changing an angle of X-ray emission θ from the X-ray tube R to the patient M so that a given point on a particular sectional plane of patient M may constantly be in the same location on the detecting plane of flat panel X-ray detector D. The angle of the X-ray tube R moving while emitting X rays may be within a selected range of angles. It is assumed here that the angle θ is within a range of +θmax (+30°) to −θmax (−30°), for example. Before picking up images of the region of interest of patient M, the input unit 10 is operated to input and determine a distance from the X-ray tube R to the flat panel X-ray detector D shown in FIG. 2, and the number of views (e.g. 50 though any desired number may be set) to be acquired, or at what pitch images are to be picked up, while the X-ray tube R and flat panel X-ray detector D are moved linearly and in parallel. Input devices such as a keyboard, mouse and/or touch panel are used as the input unit 10. The above X-ray tube R corresponds to the radiation source in this invention.

The input unit 10, driver 30 and data processor 50 are connected to the radiography controller 20. The radiography controller 20 controls the driver 30 and data processor 50 based on information inputted from the input unit 10. The contents of control will be described hereinafter in relation to each controlled component.

As shown in FIG. 2, the driver 30 drives the X-ray tube R and flat panel X-ray detector D opposed to each other across the patient M, the X-ray tube R moving linearly in the first direction, and the flat panel X-ray detector D synchronously therewith moving linearly in the second direction counter to the first direction. The X-ray tube R and flat panel X-ray detector D in the linear parallel movement scan the patient to pick up images thereof intermittently while changing the X-ray emission angle from the X-ray tube R to the patient M so that a given point on a particular sectional plane of patient M may constantly be in the same location on the detecting plane of flat panel X-ray detector D. At this time, the detecting plane of flat panel X-ray detector D is maintained parallel to the sectional plane of patient M. However, the X-ray tube R and flat panel X-ray detector D may be opposed to each other, such that the center point of X rays in the form of a cone beam emitted from the X-ray tube R toward the patient M always passes through the center point O of a particular sectional plane of the patient M, and impinges on the center point of the detecting plane of flat panel X-ray detector D in a direction perpendicular thereto. The above driver 30 corresponds to the scanning device in this invention.

The image acquire station 40 includes a top board T for supporting the patient M, the X-ray tube R for emitting X rays in the form of a cone beam toward the patient M, and the flat panel X-ray detector D for detecting X rays transmitted through the patient M.

Figure 3:
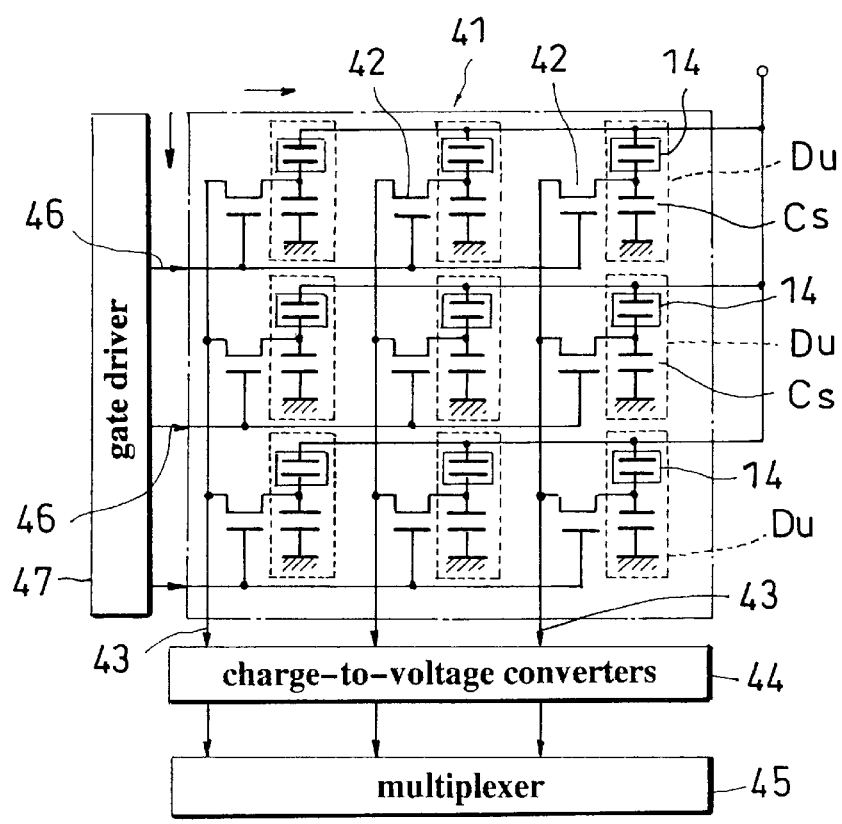
FIG. 3 is a view showing a construction of a flat panel X-ray detector.

The flat panel X-ray detector D is the type that detects fluoroscopic images of the patient M produced by the X-ray emission from the X-ray tube R, and converts the image data into electric signals for output as X-ray detection signals. As shown in FIG. 3, the X-ray detector D is in the form of a two-dimensional matrix with numerous detecting elements Du arranged in a crisscross pattern. The detecting elements Du of the flat panel X-ray detector D in this embodiment are arranged in a square matrix, e.g. 1,024 arranged horizontally (i-rows) and 1,024 arranged vertically (j-columns). For expediency of description, the square matrix is assumed here to have 1,000 detecting elements Du arranged horizontally and 1,000 detecting elements Du arranged vertically. FIG. 3 shows a matrix arrangement of only nine elements Du, i.e. 3 horizontally and 3 vertically. As distinct from an image intensifier which must have a circular detecting plane, the flat panel X-ray detector D having a rectangular plane is useful in that it may have a square detecting plane suitable for detecting images of large sites such as the chest and abdomen.

Figure 4:
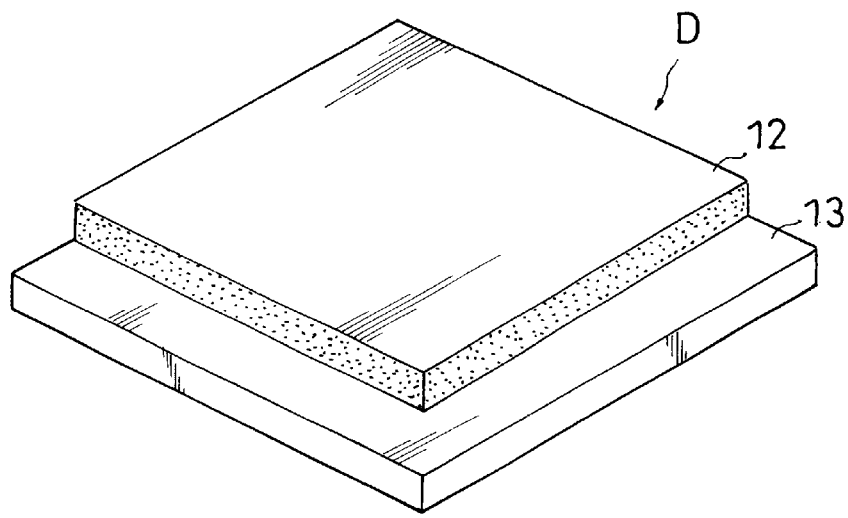
FIG. 4 is a perspective view showing an outline of the flat panel X-ray detector.

As shown in FIG. 4, the flat panel X-ray detector D has a laminated structure, and includes an X-ray converting layer 12 for converting incident X rays into electric charge or light, and a detecting array layer 13 having a matrix arrangement of elements for detecting the charge or light generated by the X-ray converting layer 12. The plane size of X-ray converting layer 12 of this flat panel X-ray detector D may be 30 cm by 30 cm, for example.

Figure 5A:
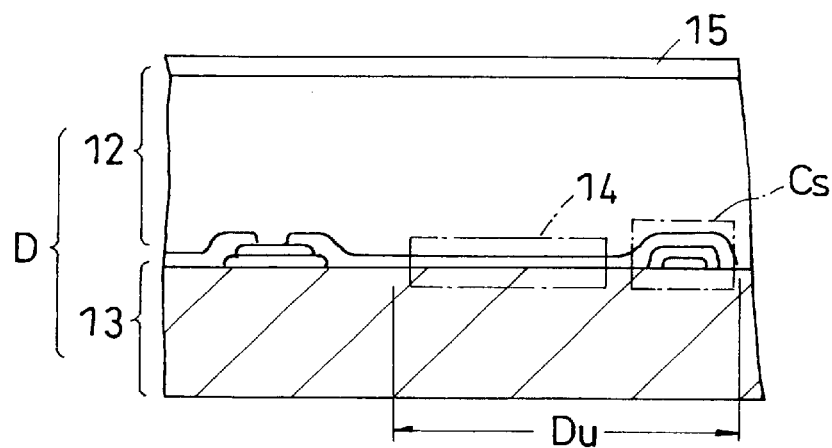
FIGS. 5A and 5B are sectional views showing a layer structure of the flat panel X-ray detector.
Figure 5B:
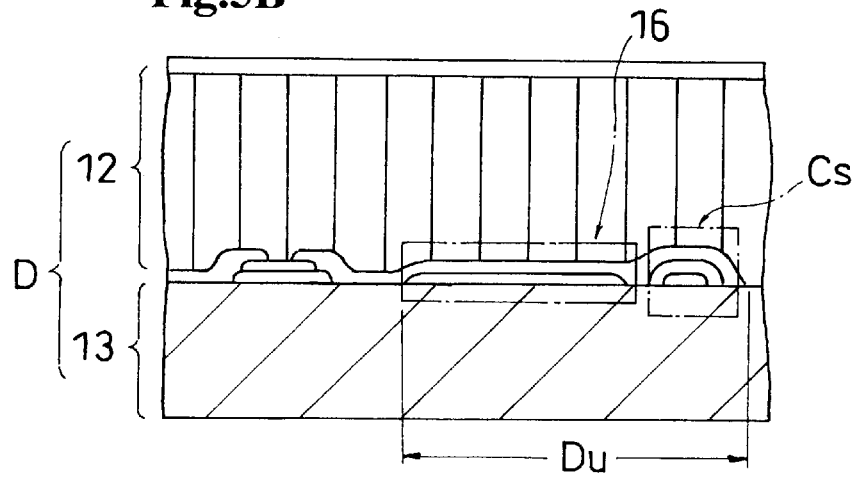

The flat panel X-ray detector D may be the direct conversion type shown in FIG. 5A or the indirect conversion type shown in FIG. 5B. In the former, direct conversion type, the X-ray converter layer 12 consists of a selenium layer, CdZnTe layer or the like for converting incident X rays directly into electric charges. The detecting array layer 13 has charge collecting electrodes formed on the surface thereof and opposed to a surface electrode 15 to act as charge detecting elements 14 for detecting the charges, and capacitors Cs for storing the charges. Each charge detecting element 14 and a part of X-ray conversion layer 12 thereover constitute one detecting element Du. In the latter, indirect conversion type, the X-ray converting layer 12 consists of a scintillator layer for converting incident X rays into light. The detecting array layer 13 has photodiodes formed on the surface thereof to act as photo detecting elements 16 for detecting the light, and capacitors Cs for storing electric charges. Each photo detecting element 16 and a part of X-ray conversion layer 12 thereover constitute one detecting element Du.

As shown in FIG. 3, the flat panel X-ray detector D includes an X-ray detector substrate 41 with the X-ray converting layer 12 and detecting array layer 13 formed thereon, the capacitors Cs for storing collected carriers (collected charges) from the carrier collecting electrodes (charge collecting electrodes) on the X-ray detector substrate 41, thin film transistors (TFT) acting as charge fetching switching elements 42, which are normally turned off, for fetching the charges stored in the capacitors Cs, and a multiplexer 45 and a gate driver 47 acting as reading circuits for i- and j-directions.

As shown in FIG. 3, the flat panel X-ray detector D has the thin film transistors acting as the switching elements 42 of detecting elements Du. The thin film transistors have sources thereof connected to vertical sense lines 43 arranged in i-direction, and gates connected to horizontal sense lines 46 arranged in j-direction. The sense lines 43 are connected to the multiplexer 45 through a group of charge-to-voltage converters (group of preamplifiers) 44. The sense lines 46 are connected to the gate driver 47. In the group of charge-to-voltage converters 44, though not shown, one charge-to-voltage converter is connected to each sense line 43.

In the flat panel X-ray detector D, scan signals are inputted to the multiplexer 45 and gate driver 47 for fetching signals. The detecting elements Du are identified by means of addresses (0 to 999 since the number of detecting elements Du is 1,000; 0 to 1023 where 1024 detecting elements Du are provided) sequentially allocated to the detecting elements Du along the i- and j-directions. Thus, the fetching scan signals serve as signals designating the addresses in the i-direction or j-direction.

In response to scan signals for the j-direction, the gate driver 47 applies a fetching voltage to the sense lines 46 arranged in the j-direction, whereby detecting elements Du are selected on a column-by-column basis. When the multiplexer 45 is switched by scan signals for the i-direction, the charges stored in the capacitors Ca of the detecting elements Du in the selected columns are outputted through the charge-to-voltage converter group 44 and then the multiplexer 45. Thus, the flat panel X-ray detector D successively outputs detection signals to the data processor 50 in real time. The above flat panel X-ray detector D corresponds to the area detector in this invention.

The construction and functions of data processor 50 will be described next. As shown in FIG. 1, the data processor 50 includes an image processor 51 for performing an image reconstruction to generate three-dimensional volume data of a region of interest from projection data (detection signals) detected in varied scan positions at the image acquire station 40, and an image information storage 52 for storing the three-dimensional volume data of the region of interest generated by the image processor 51. Specific functions of the image processor 51 and image information storage 52 will be described hereinafter.

A series of processing steps for the image reconstruction to generate the three-dimensional volume data of the region of interest will be outlined with reference to FIGS. 1 and 2. As shown in FIG. 2, the X-ray tube R and flat panel X-ray detector D are opposed to each other across the patient M. The X-ray tube R is driven to move linearly in the first direction, and the flat panel X-ray detector D synchronously therewith to move linearly in the second direction counter to the first direction. The X-ray tube R and flat panel X-ray detector D in the linear parallel movement scan the patient M to pick up images thereof intermittently while changing the X-ray emission angle from the X-ray tube R to the patient M so that a given point on a particular sectional plane of patient M may constantly be in the same location on the detecting plane of flat panel X-ray detector D. This operation acquires a group of projection data of the region of interest of patient M detected in varied scan positions. Next, the group of projection data is subjected to a filtering process to be described hereinafter. Next, the projection data filtered are individually subjected to a predetermined back projection (BP) to be described hereinafter, to generate a BP image (three-dimensional volume data). The operator may observe an image of any sectional plane (seen in the direction of X-axis) selected from the three-dimensional volume data.

Figure 6:
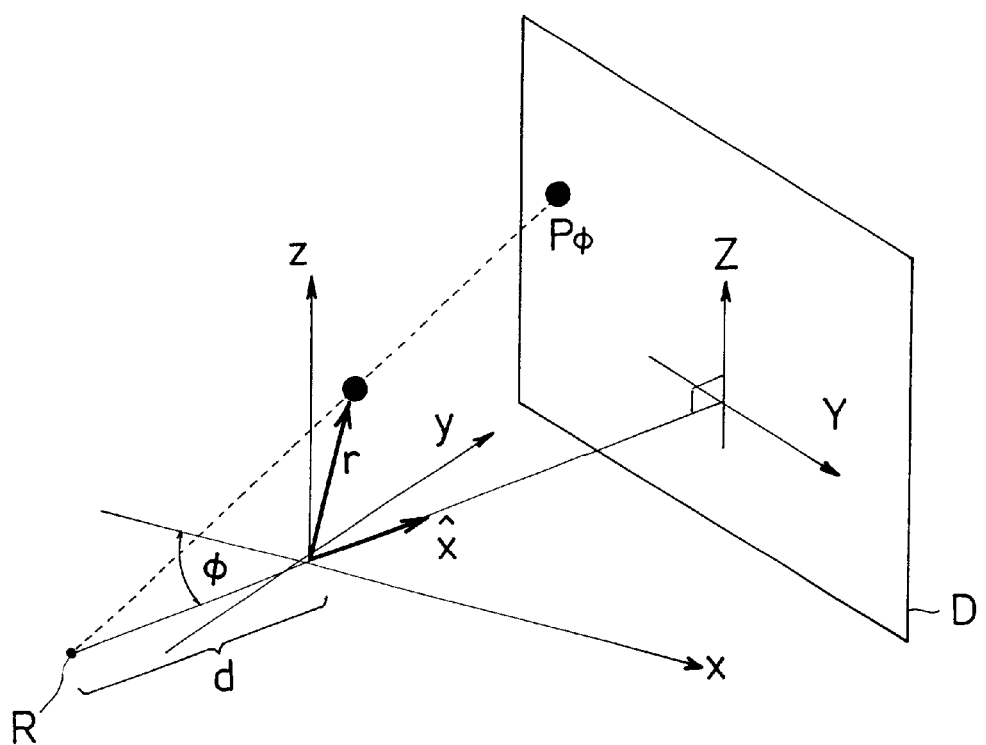
FIG. 6 is a schematic view illustrating an algorithm for an FBP method in the first embodiment.

The algorithm of the above-noted FBP (Filtered Back Projection) method is expressed by equations (1) and (2) set out below. Three-dimensional volume data f(r) is thereby reconstructed from a plurality of projection data $P_\Phi$ obtained from different angles (see FIG. 6).

$$f(\vec{r}) = \frac{1}{4\pi^2} \oint W \int_{-\infty}^{\infty} g_y(Y(\vec{r}) - Y') P_\Phi(Y', Z(\vec{r})) dY' d\Phi \quad (1)$$

$$W = \frac{d^2}{(d + \vec{r} \cdot \hat{x}')^2} \quad (2)$$

In the above equations, f(r) is pixel data for position r in the three-dimensional volume data reconstructed. Y(r) and Z(r) are coordinates of a point where a pixel in position r is projected on the detecting plane of flat panel X-ray detector D. $P_\Phi$ is projection data on the detecting plane of flat panel X-ray detector D for projection angle $\Phi$. $g_y$ is called a filter function of Filtered Back Projection which is an $|\omega|$ (absolute value omega) filter function to be described hereinafter. W is a factor for correcting influences of beam divergence.

As shown in FIG. 1, the image processor 51 includes a filtering unit 53 for performing a predetermined filtering process on the group of projection data acquired by radiography, and a back projection unit 54 for performing a predetermined back projection (BP) individually on the projection data filtered, to generate a BP image (three-dimensional volume data).

The filtering unit 53 performs the predetermined filtering process on the group of projection data. A filtering process (i.e. an $|\omega|$ (absolute value omega) filtering process shown in FIG. 7) performed in a Fourier space will be described here. The |ω| filtering process performed by the filtering unit 53 will be described hereinafter.

The filtering unit 53 includes a one-dimensional Fourier transform unit for performing a one-dimensional Fourier transform sideways on each i-row of flat panel X-ray detector D to generate an image in Fourier space SCF (i, ω)), an |ω| filtering unit for applying an |ω| filter to the image in Fourier space SCF (i, ω) resulting from the one-dimensional Fourier transform, and a one-dimensional inverse Fourier transform unit for performing a one-dimensional inverse Fourier transform of the image in Fourier space SCF' (i, ω) filtered by |ω| filter function by the |ω| filtering unit to put the image back to real space data.

Figure 7:
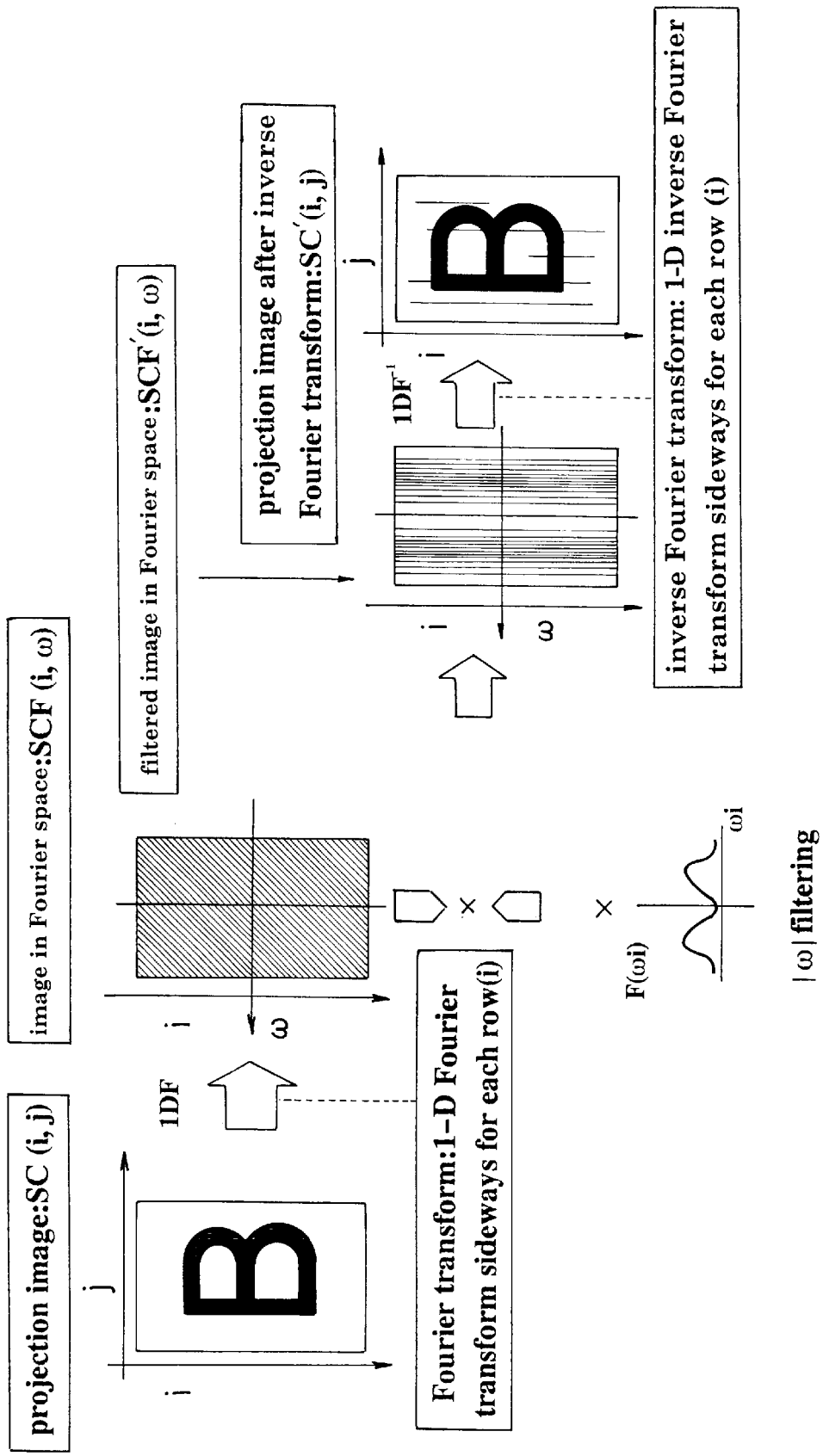
FIG. 7 is a schematic view illustrating a series of processing steps performed by a filtering unit in the first embodiment.

As shown in FIG. 7, the |ω| filtering unit includes a filter for suppressing high frequency noise by isotropically reducing the high frequency regions in the i-direction of the image in Fourier space SCF (i, ω) resulting from the one-dimensional Fourier transform, and an |ω| filter dependent on a data collection scan mode. The filter dependent on a data collection scan mode suppresses DC components to reduce artifacts caused by the DC components being emphasized, when the filtered image in Fourier space SCF' (i, ω) is subjected to the one-dimensional inverse Fourier transform.

The meaning of the filtering process performed in the one-dimensional Fourier space will be described now. The filtering process performed in the one-dimensional Fourier space is mathematically expressed by the following equation (3):

$$SCF'(i, ω)=SCF(i, ω) \times M(ωi) \qquad (3)$$

where SCF' (i, ω) is the filtered one-dimensional image in Fourier space, and M(ωi) is a function representing the specific of the filter of the above |ω| filtering unit.

M (ωi) is expressed by the following equation (4) as a product of two functions representing the specific of the filter:

$$M(ωi)=Mi(ωi) \cdot Mω(ωi) \qquad (4)$$

A typical example of each filter function system shown in the equation (4) will be described hereinafter.

Figure 8A:
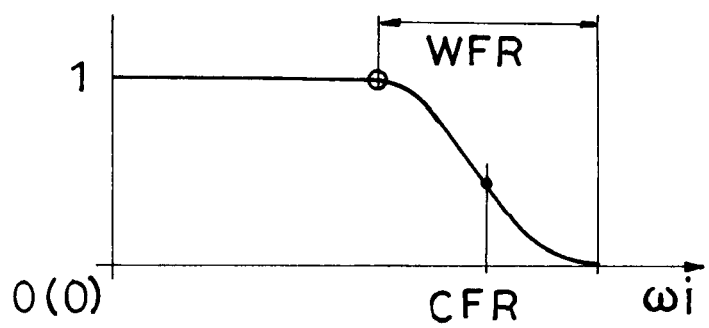
FIGS. 8A and 8B are characteristic views showing filter functions of the filtering unit.

Mi (ωi) has the specific of the filter as shown in FIG. 8A, which is expressed by the following equations (5)–(7):

$$Mi(ωi)=1 \text{ (where } ωi<CFR-WFR/2) \qquad (5)$$

$$Mi(ωi)=\{1-\sin((ωi-CFR) \cdot π/WFR)\}/2 \text{ (where } CFR-WFR/2<ωi<CFR+WFR/2) \qquad (6)$$

$$Mi(ωi)=0 \text{ (where } CFR+WFR/2<ωi) \qquad (7)$$

However, the function has a sine wave form with high frequency components smoothly attenuating as shown in FIG. 8A. CFR is a cutoff frequency, and WFR is a total transition frequency width of filter strength (see FIG. 8A). This Mi (ωi) deletes high frequency components from the one-dimensional Fourier space.

Figure 8B:
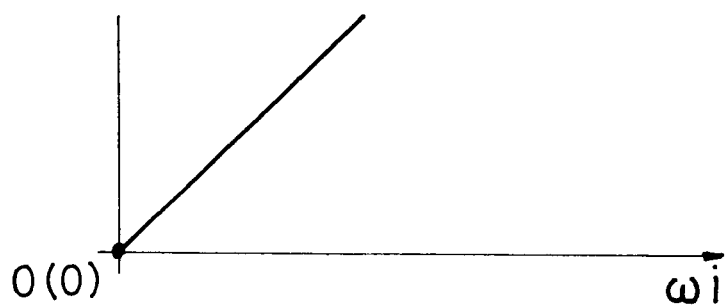

Mω (ωi) has the specific of the filter shown in FIG. 8B, which is expressed by the following equation (8):

$$i \, Mω(ωi)=|ωi| \qquad (8)$$

FIGS. 8A and 8B show only the characteristics in the plus direction along the horizontal axis. The characteristics in the minus direction along the horizontal axis are omitted since these are in linear symmetry with the characteristics in the plus direction about the vertical axis.

Reverting to FIG. 7, the one-dimensional inverse Fourier transform unit performs a one-dimensional inverse Fourier transform of the image in Fourier space SCF' (i, ω) filtered by |ω| filter function by the |ω| filtering unit to put the image back to real space data and generate a inverse Fourier transformed projection image SC' (i, j).

Figure 9:
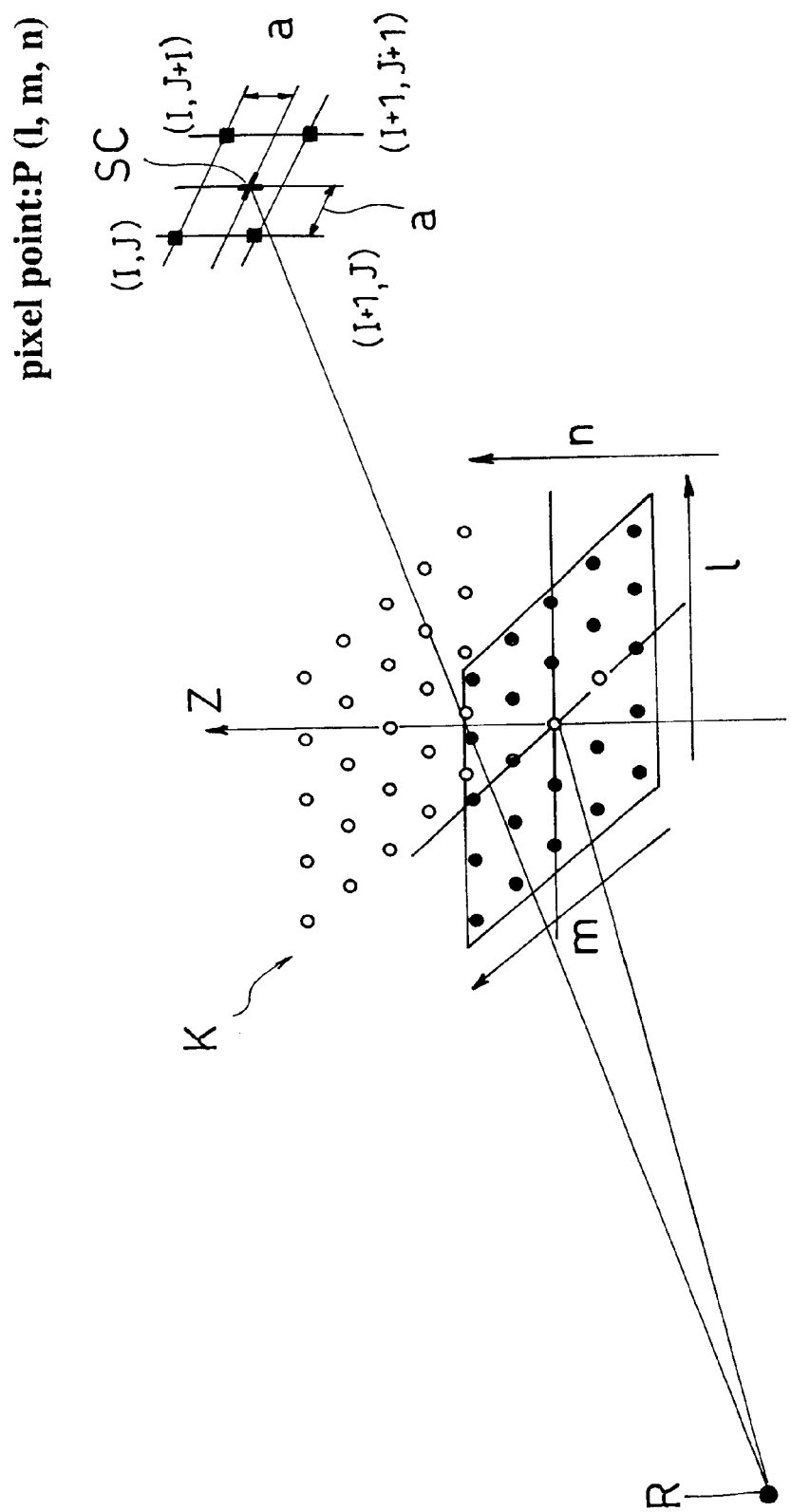
FIG. 9 is a schematic view illustrating filtered projection data projected back to a virtual three-dimensional lattice.

Next, the back projection unit 54 performs a predetermined back projection (BP) of individual filtered projection data to generate a BP image (three-dimensional volume data). Specifically, an image reconstruction is performed to generate three-dimensional volume data of the region of interest of patient M by projecting the group of projection data of the region of interest detected in the varied scan positions and filtered, back to predetermined lattice points of a three-dimensional lattice K virtually set to the region of interest as shown in FIG. 9.

Specifically, a back projection based on a computation for linear interpolation is carried out according to the following equation (9):

$$I_n(l, m, n)=I_{n-1}(l, m, n)+\{W_{11} \cdot SC'(I, J)+W_{12} \cdot SC'(I, J+1)+ W_{21} \cdot SC'(I30\ 1, J)+W_{22} \cdot SC'(I+1, J+1)\} \qquad (9)$$

where $I_n$ (l, m, n) is an accumulation of back projection, $I_{n-1}$ (l, m, n) is an accumulation of back projection made by preceding steps, and SC' is projection data resulting from a inverse Fourier transform done after a filtering process.

Pixel spacing of the projection image is standardized to 1, and weight functions in a multiplication weighting method as in the following equations (10)–(13) are used:

$$W_{11}=(1-a_z) \cdot (1-a_y) \qquad (10)$$

$$W_{12}=(1-a_z) \cdot a_y \qquad (11)$$

$$W_{21}=a_z \cdot (1-a_y) \qquad (12)$$

$$W_{22}=a_z \cdot a_y \qquad (13)$$

A similar back projection is performed on the remaining predetermined lattice points of three-dimensional lattice K. Further, a similar back projection is performed for each scan position, i.e. over the range of +θmax (+30°) to −θmax (−30°) to generate a BP image (three-dimensional volume data).

The image information storage 52 stores the three-dimensional volume data generated by the back projection unit 54. When the input unit 10 is operated to select image information of any given slice, the image information storage 52 outputs the image information of that slice to the monitor 60.

The monitor 60 has a function to display selected image information stored in the image information storage 52.

In the first embodiment described above, the back projection unit 54 projects projection data detected in varied scan positions back to predetermined lattice points of the three-dimensional lattice K virtually set to the region of interest of patient M radiographed. In this way, an image reconstruction is carried out to generate three-dimensional volume data of the region of interest. This invention does not use the conventional method in which two-dimensional sectional image data is generated by adding detection signals to superimpose, on a single plane, a plurality of projection images acquired by radiography from varied angles (i.e. projection images acquired from varied scan positions). Instead, an image reconstruction is carried out to generate three-dimensional volume data of the region of interest by projecting projection images acquired from varied scan positions back to predetermined lattice points of the three-dimensional lattice K. Three-dimensional volume data of the region of interest may be generated without performing radiography a plurality of times. Thus, three-dimensional volume data of the region of interest of patient M is generated quickly. In addition, the burden of exposure may be reduced for the patient M.

One of the X-ray tube R and flat panel X-ray detector D is driven to move linearly in the first direction, and the other synchronously therewith to move linearly in the second direction counter to the first direction. Thus, the X-ray tube R and flat panel X-ray detector D are moved linearly and parallel to each other with the patient M placed in between. The X-ray tube R and flat panel X-ray detector D in the linear parallel movement may scan a region of patient M to pick up images thereof, thereby performing radiography for an image reconstruction to generate three-dimensional volume data of the region of interest.

The filtering unit 53 applies an $|\omega|$ filter to Fourier space data resulting from a one-dimensional Fourier transform of the projection images acquired from the varied scan positions. A inverse Fourier transform may therefore be carried out properly without emphasizing DC components of the Fourier space data resulting from the $|\omega|$ filtering. This produces the effect of reducing artifacts caused by the DC components being emphasized.

In the first embodiment described above, the filtering unit 53 applies an $|\omega|$ filter to the group of projection data in the Fourier space. The $|\omega|$ filtering process in the Fourier space is mathematically equivalent to a convolution process in the real space. Thus, the $|\omega|$ filtering in the Fourier space by the filtering unit 53 includes a convolution process in the real space. That is, a convolution process may be performed in the real space.

Figure 10A:
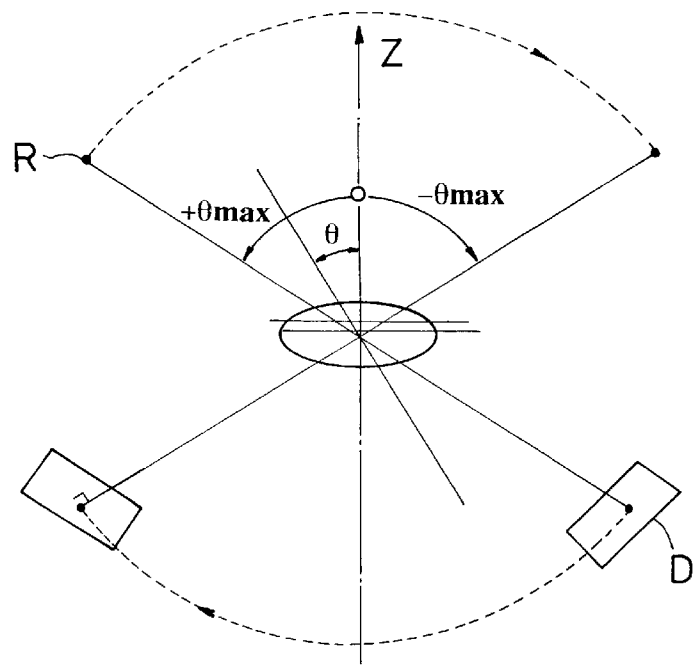
FIGS. 10A and 10B are views showing other image pickup modes of the X-ray radiographic apparatus.

In the first embodiment described above, the driver 30 drives the X-ray tube R and flat panel X-ray detector D to move linearly and parallel to each other. Various other scan modes may be employed as described hereunder. As shown in FIG. 10A, for example, two arcuate tracks may be set on a circumferential track around the patient M to be opposed to each other across the patient M. The X-ray tube R is moved on one of the arcuate tracks, while the flat panel X-ray detector D is moved on the other arcuate track in synchronism therewith to maintain a fixed distance from the X-ray tube R, to perform what is known as arcuate scanning. Thus, by causing the X-ray tube R and flat panel X-ray detector D to move separately and arcuately and scan the patient M lying in between, radiography may be carried out to enable an image reconstruction to generate three-dimensional volume data of a region of interest of patient M.

As shown in 10B, the X-ray tube R may be driven to revolve in one of parallel planes opposed to each other across the patient M, and the flat panel X-ray detector D to revolve synchronously therewith in the other parallel plane in the direction counter to the direction of revolution of X-ray tube R, to perform what is known as circular scanning. Thus, the X-ray tube R and flat panel X-ray detector D are revolved in the separate parallel planes opposed to each other across the patient M. Radiography may thereby be performed for an image reconstruction to generate three-dimensional volume data of the region of interest of patient M.

Figure 10B:
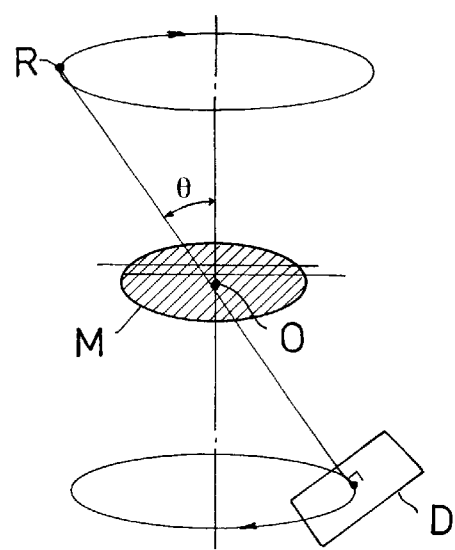

As shown in FIGS. 10A and 10B, the X-ray tube R and flat panel X-ray detector D are opposed to each other, such that the center point of X rays emitted in a cone beam from the X-ray tube R constantly passes through the center point O of a particular sectional plane of patient M and impinges on the center point of and perpendicular to the detecting plane of flat panel X-ray detector D. The detecting plane of flat panel X-ray detector D may be maintained parallel to the sectional planes of patient M.

Though the X-ray tube R and flat panel X-ray detector D are moved in scanning action, the X-ray tube R may be fixed, with the flat panel X-ray detector D and patient M movable during the scanning, for example. Alternatively, the flat panel X-ray detector D may be fixed, with the X-ray tube R and patient M movable during the scanning. Thus, scanning may be performed by moving any two of the X-ray tube R, flat panel X-ray detector D and patient M.

<Second Embodiment>

Figure 11:
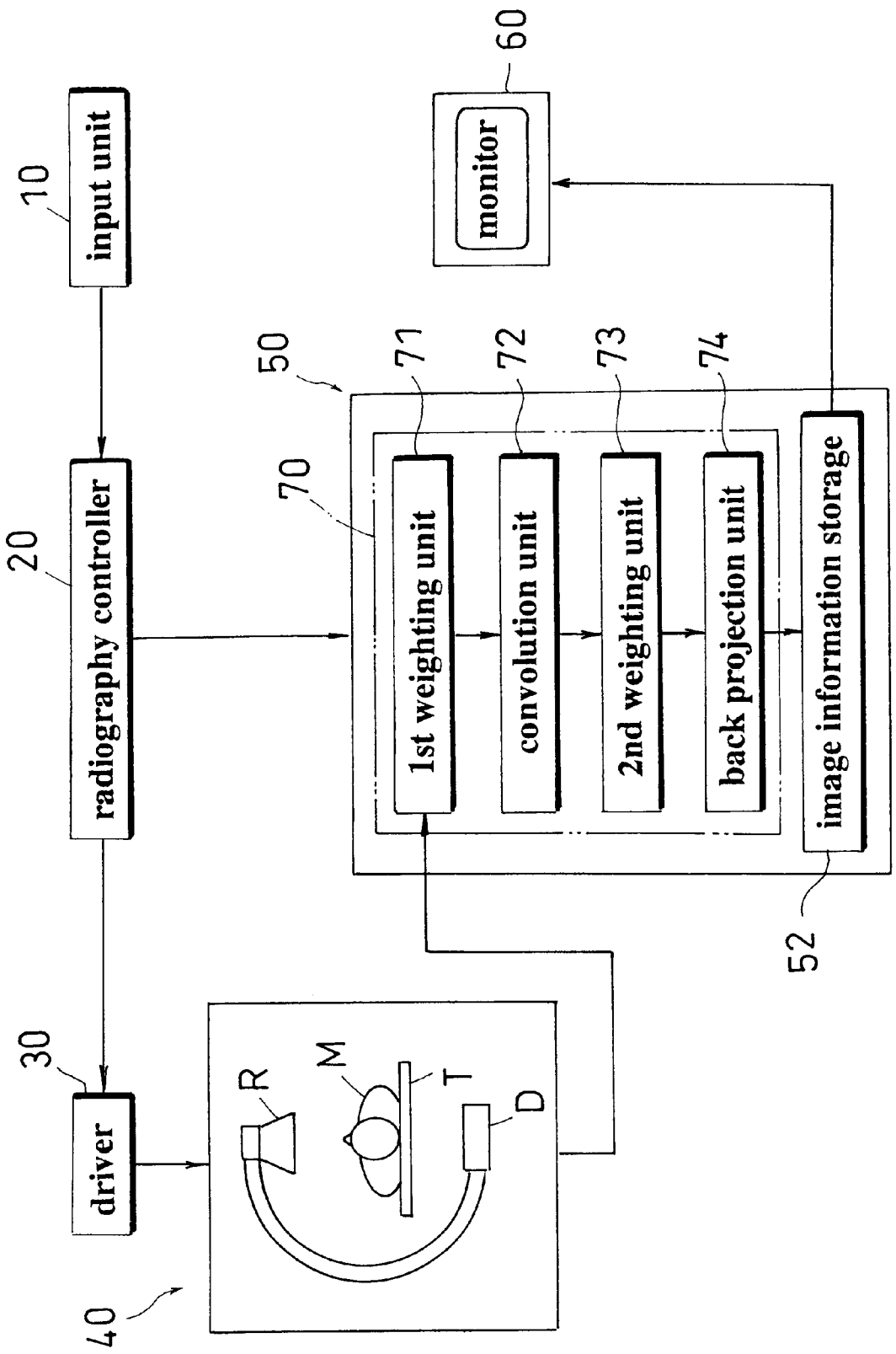
FIG. 11 is a block diagram of an X-ray radiographic apparatus in a second embodiment.

A non-CT type X-ray radiographic apparatus in a second embodiment of this invention will be described next with reference to the drawings. FIG. 11 is a block diagram of the X-ray radiographic apparatus in the second embodiment of this invention.

This X-ray radiographic apparatus differs from the apparatus in the first embodiment in that an image processor 70 is employed in place of the image processor 51. The other aspects of construction remain the same as in the first embodiment. Thus, like reference numerals will be used to identify like parts, and the image processor 70 characterizing the second embodiment will be described in detail hereinafter.

In the second embodiment, the X-ray tube R and flat panel X-ray detector D are operable in the following scan mode.

Figure 12A:
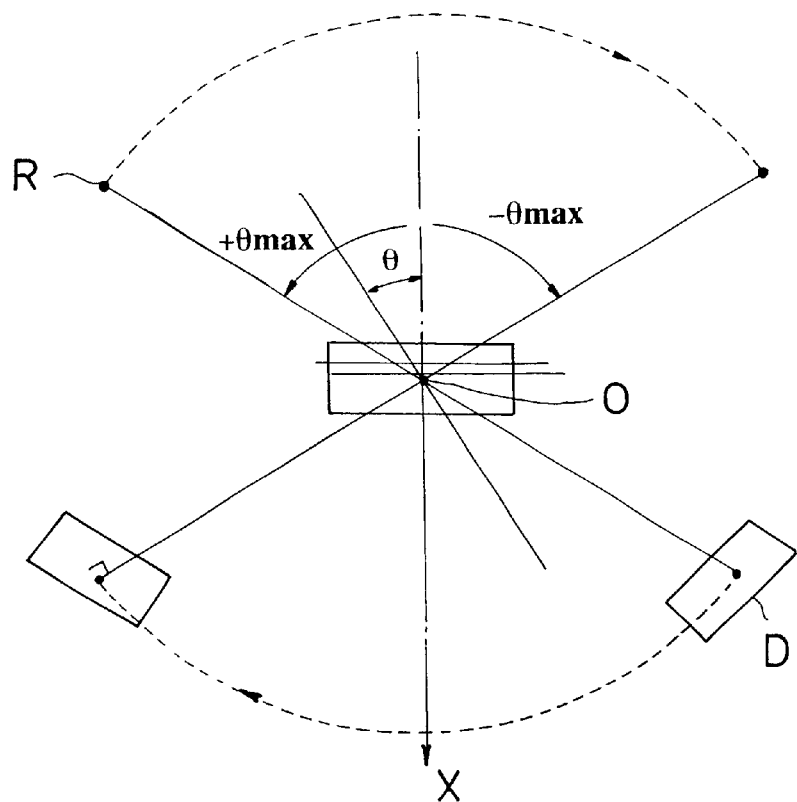
FIG. 12A is a schematic side view showing one scan mode of an X-ray tube and a flat panel X-ray detector in the second embodiment.
Figure 12B:
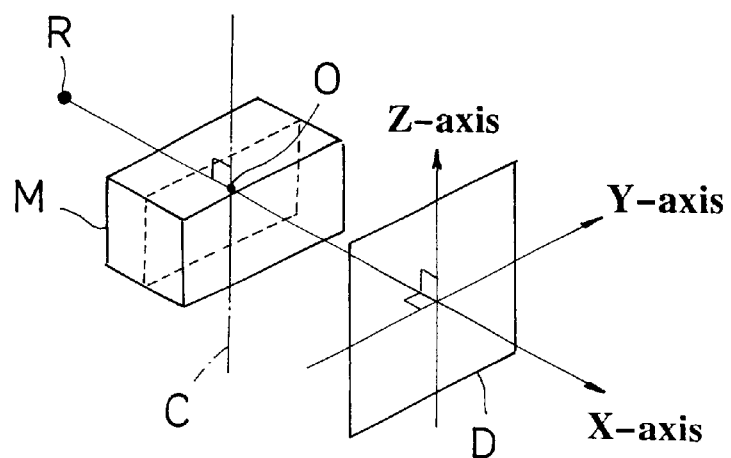
FIG. 12B is a schematic perspective view of what is shown in FIG. 12A.

Referring to FIGS. 12A and 12B, two arcuate tracks are set on a circumferential track around the patient M to be opposed to each other across the patient M. The X-ray tube R is moved on one of the arcuate tracks, while the flat panel X-ray detector D is moved on the other arcuate track in synchronism therewith to maintain a fixed distance from the X-ray tube R, to perform arcuate scanning. Radiography is performed intermittently while changing an angle of X-ray emission $\theta$ from the X-ray tube R to the patient M so that a given point on a particular sectional plane of patient M may constantly be in the same location on the detecting plane of flat panel X-ray detector D. The X-ray emission angle $\theta$ may be within a selected range of angles. It is assumed here that the angle $\theta$ is within a range of $+\theta\text{max}$ ($+30°$) to $-\theta\text{max}$ ($-30°$), for example. Before picking up images of the region of interest of patient M, the input unit 10 is operated to input and determine a distance from the X-ray tube R to the flat panel X-ray detector D shown in FIGS. 12A and 12B, and the number of views (e.g. 50 though any desired number may be set) to be acquired, or at what pitch images are to be picked up, while the X-ray tube R and flat panel X-ray detector D are moved arcuately.

The driver 30 drives the X-ray tube R and flat panel X-ray detector D opposed to each other across the patient M as shown in FIGS. 12A and 12B, the X-ray tube R moving on one of the arcuate tracks, and the flat panel X-ray detector D synchronously therewith moving on the other arcuate track to maintain a fixed distance from the X-ray tube R, to perform arcuate scanning. At this time, the X-ray tube R and flat panel X-ray detector D are opposed to each other such that the center point of X rays in the form of a cone beam emitted from the X-ray tube R toward the patient M always passes through the center point O of a particular sectional plane of the patient M (see FIG. 12B), and impinges on the center point of the detecting plane of flat panel X-ray detector D in a direction perpendicular thereto.

The construction and functions of data processor 50 will be described next. As shown in FIG. 11, the data processor 50 includes the image processor 70 for performing an image reconstruction to generate three-dimensional volume data of a region of interest from projection data (detection signals) detected in varied scan positions at the image acquire station 40, and an image information storage 52 for storing the three-dimensional volume data of the region of interest generated by the image processor 70. Specific functions of the image processor 70 and image information storage 52 will be described hereinafter. This image processor 70 enables application of the Feldkamp method which is a cone beam CT reconstruction technique, to a non-CT type image reconstruction technique. In the CT reconstruction technique, transmitted images are acquired by driving the X-ray tube R and flat panel X-ray detector D opposed to each other across the patient to make one revolution (at least a half revolution) about the body axis of the patient, the X-ray tube R emitting X-rays in a cone beam and the flat panel X-ray detector D detecting X rays transmitted through the patient. Then, an image reconstruction is carried out based on the transmitted images acquired while one revolution (at least a half revolution) about the body axis of the patient. On the other hand, the non-CT image reconstruction technique does not cause the X-ray tube and flat panel X-ray detector D to make a half or more revolution about the body axis of the patient.

A series of processing steps for the image reconstruction to generate the three-dimensional volume data of the region of interest, based on the Feldkamp method made applicable to the non-CT image reconstruction technique, will be outlined with reference to FIGS. 11 and 12. As shown in FIG. 12, two arcuate tracks are set on a circumferential track about a center axis C extending substantially through the center of the region of interest of patient M, to be opposed to each other across the patient M. The X-ray tube R is moved on one of the arcuate tracks, while the flat panel X-ray detector D is moved on the other arcuate track in synchronism therewith to maintain a fixed distance from the X-ray tube R, to perform arcuate scanning. This operation acquires a group of projection data of the region of interest of patient M detected in varied scan positions. Next, the projection data are individually subjected to a first weighting process described hereinafter. Then, a predetermined convolution process described hereinafter is performed on the projection data resulting from the first weighting process. Next, a second weighting process described later is performed on the projection data resulting from the convolution process. Next, the projection data resulting from the second weighting process are individually subjected to a predetermined back projection (BP) to be described hereinafter, to generate a BP image (three-dimensional volume data). In this way, an image reconstruction is carried out to generate three-dimensional volume data of the region of interest. The operator may observe an image of any sectional plane (seen in the direction of X-axis) selected from the three-dimensional volume data.

Figure 13:
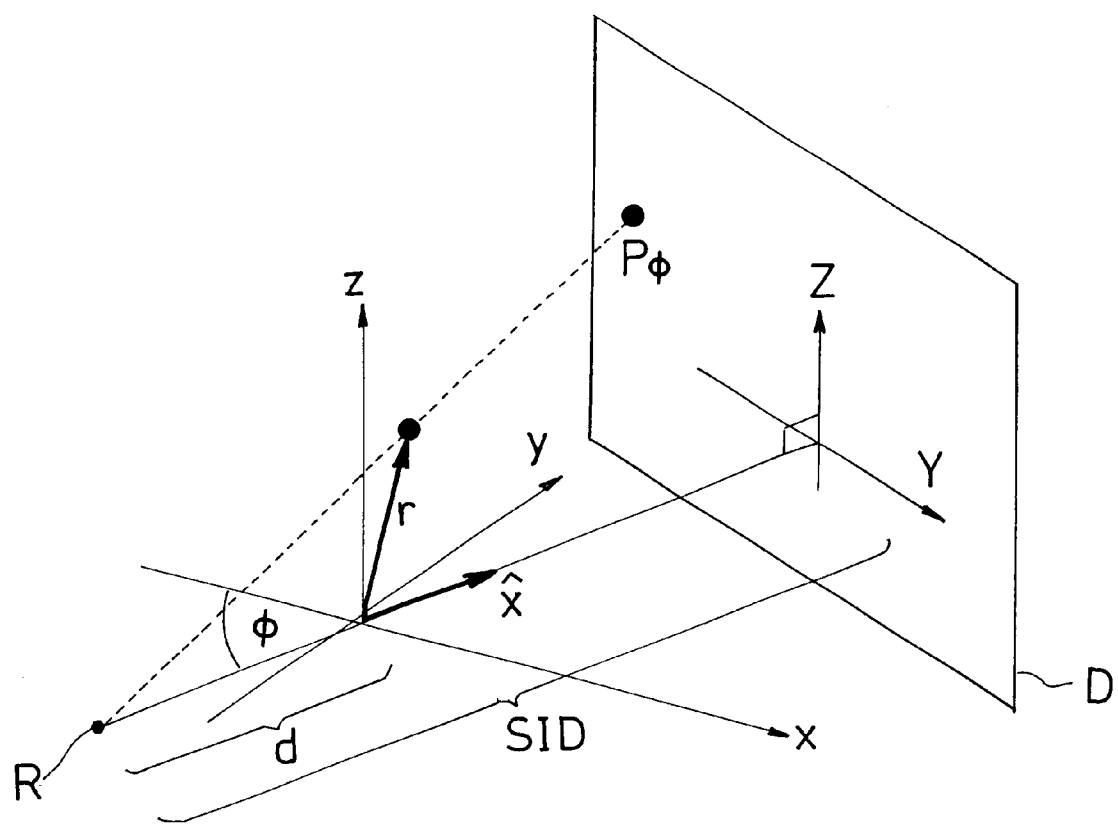
FIG. 13 is a schematic view illustrating a Feldkamp algorithm used in the second embodiment.

An algorithm of the Feldkamp method noted above is expressed by the following equations (21)–(23). Three-dimensional volume data f(r) is thereby reconstructed from a plurality of projection data $P_\Phi$ obtained from different angles (see FIG. 13).

$$f(\vec{r}) = \frac{1}{4\pi^2} \oint W_2 \int_{-\infty}^{\infty} g_y(Y(\vec{r}) - Y') P_\Phi(Y', Z(\vec{r})) W_1 dY' d\Phi \quad (21)$$

$$W_1 = \frac{d}{\sqrt{d + Y'^2 + Z^2}} \quad (22)$$

$$W_2 = \frac{d^2}{(d + \vec{r} \cdot \hat{x}')^2} \quad (23)$$

In the above equations, f(r) is pixel data for position r in the three-dimensional volume data reconstructed. Y(vr) and Z(vr) are coordinates of a point where a pixel in position r is projected on the detecting plane of flat panel X-ray detector D. The small letter v above means "vector". The small letter "v" will be used hereinafter to represent vector. $P_\Phi$ is projection data on the detecting plane of flat panel X-ray detector D for projection angle $\Phi$. $g_y$ is called a filter function of Filtered Back Projection which is $|\omega|$ (absolute value omega) filter function to be described hereinafter. $W_1$ and $W_2$ are factors for correcting influences of beam divergence. $W_1$ is a factor relating to the first weighting process to be described hereinafter. $W_2$ is a factor relating to the second weighting process to be described hereinafter.

As shown in FIG. 11, the image processor 70 includes a first weighting unit 71 for performing the first weighting process individually on the group of projection data acquired by radiography, a convolution unit 72 for performing the predetermined convolution process on each projection data after the first weighting process, a second weighting unit 73 for performing the second weighting process on each projection data after the convolution process, and a back projection unit 74 for performing the predetermined back projection (BP) individually of the projection data after the second weighting process to generate a BP image (three-dimensional volume data).

Figure 14:
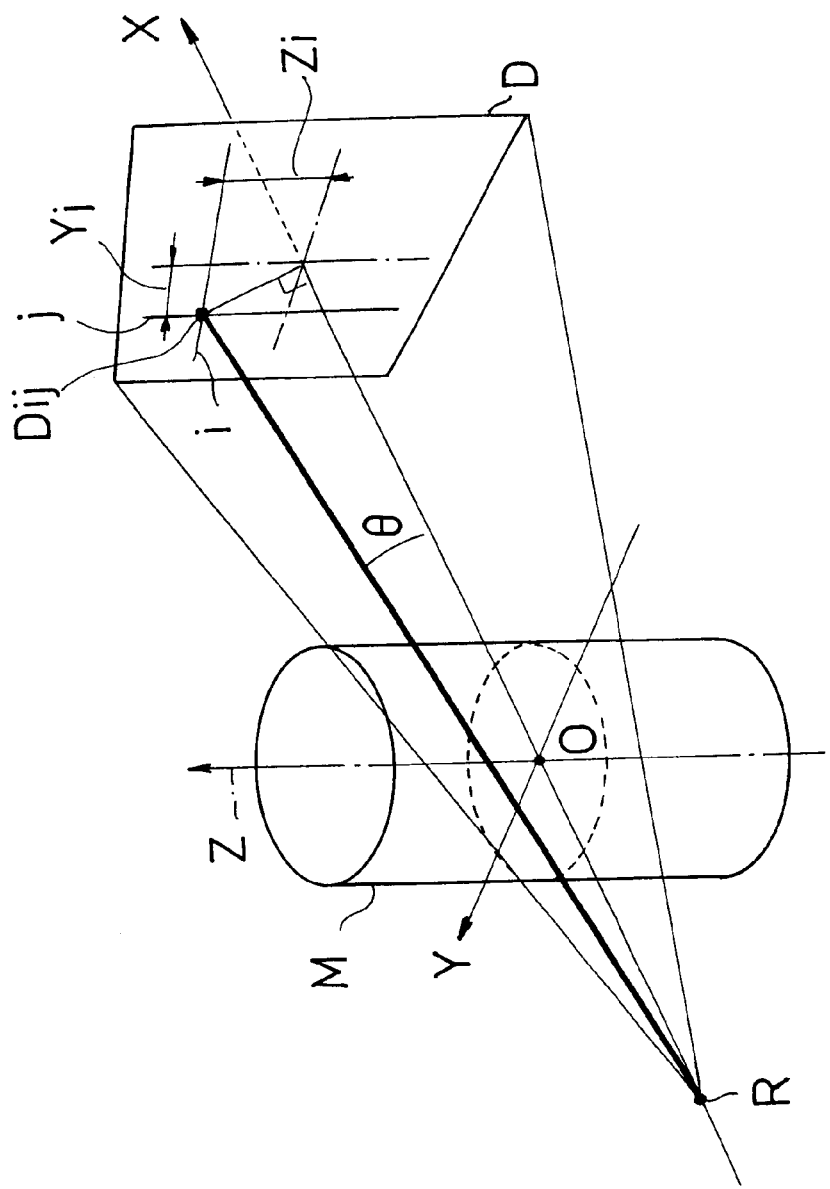
FIG. 14 is a schematic view illustrating a cosine correction by a first weighting unit in the second embodiment.

The first weighting unit 71 performs the first weighting process individually on the group of projection data acquired by radiography. Specifically, as shown in FIG. 14, the first weighting unit 71 performs, on the projection data, a weighting process based on the following equation (24):

$$\cos\theta = SID/(SID^2 + Yj^2 + Zj^2)^{1/2} \quad (24)$$

Figure 15:
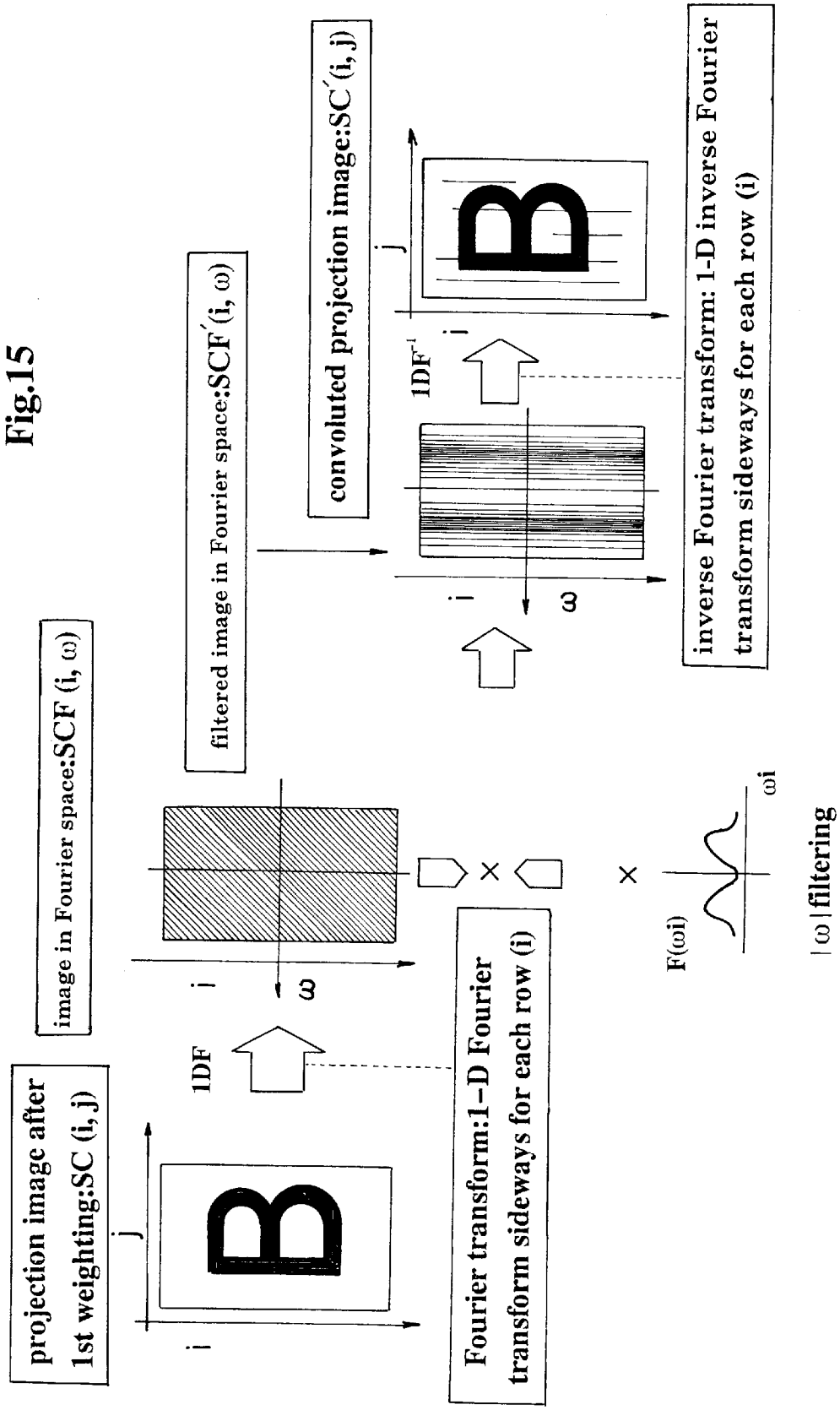
FIG. 15 is a schematic view illustrating a series of processing steps executed by a convolution unit in the second embodiment.

That is, the weighting process is performed by multiplying each pixel by $\cos\theta$ of equation (24). For example, a weighted value of pixel Dij is derived from Yj·cos θ. As shown in FIG. 14, the center point of X rays in the form of a cone beam emitted from the X-ray tube R toward the patient M always passes through the center point O of a particular sectional plane of the patient M (which is also a point on the center axis C of the circumferential track), and impinges on the center point of the detecting plane of flat panel X-ray detector D in a direction perpendicular thereto. In this way, projection data after the first weighting process is calculated (FIG. 15 shows this as "projection image after 1st weighting: SC (i, j)").

The convolution unit 72 performs the predetermined convolution process on each projection data after the first weighting process, i.e. the projection image after 1st weighting: SC (i, j). The convolution process performed in the real space is equivalent to a filtering process in the Fourier space. Thus, for expediency of description, the above predetermined convolution process will be described as a filtering process performed in the Fourier space ($|\omega|$ filtering (absolute value omega filtering shown in FIG. 15). The $|\omega|$ filtering process performed by the convolution unit 72 will be described hereinafter.

The convolution unit 72 includes a one-dimensional Fourier transform unit for performing a one-dimensional Fourier transform sideways on each i-row of flat panel X-ray detector D to generate an image in Fourier space SCF (i, ω), a filtering unit for applying an $|\omega|$ filter to the image in Fourier space SCF (i, ω) resulting from the one-dimensional Fourier transform, and a one-dimensional inverse Fourier transform unit for performing a one-dimensional inverse Fourier transform of the image in Fourier space SCF' (i, ω) filtered by |ω| filter function by the |ω| filtering unit to put the image back to real space data.

As shown in FIG. 15, the filtering unit includes a filter for suppressing high frequency noise by isotropically reducing the high frequency regions in the i-direction of the image in Fourier space SCF (i, ω) resulting from the one-dimensional Fourier transform, and an |ω| filter dependent on a data collection scan mode. The filter dependent on a data collection scan mode suppresses DC components to reduce artifacts caused by the DC components being emphasized, when the filtered image in Fourier space SCF' (i, ω) is subjected to the one-dimensional inverse Fourier transform.

The meaning of the filtering process performed in the one-dimensional Fourier space will be described now. The filtering process performed in the one-dimensional Fourier space is mathematically expressed by the following equation (25):

$$SCF'(i, \omega) = SCF(i, \omega) \times M(\omega i) \quad (25)$$

where SCF' (i, ω) is the filtered one-dimensional image in Fourier space, and M (ωi) is a function representing the specific of the filter of the above filtering unit.

M (ωi) is expressed by the following equation (26) as a product of two functions representing the specific of the filter:

$$M(\omega i) = Mi(\omega i) \cdot M\omega(\omega i) \quad (26)$$

A typical example of each filter function system shown in the equation (26) will be described hereinafter.

M (ωi) has the specific of the filter as shown in FIG. 8A, which is expressed by the following equations (27)–(29):

$$Mi(\omega i) = 1 \text{ (where } \omega i < CFR - WFR/2) \quad (27)$$

$$Mi(\omega i) = \{1 - \sin((\omega i - CFR) \cdot \pi / WFR)\}/2 \text{ (where } CFR - WFR/2 < \omega i < CFR + WFR/2) \quad (28)$$

$$Mi(\omega i) = 0 \text{ (where } CFR + WFR/2 < \omega i) \quad (29)$$

However, the function has a sine wave form with high frequency components smoothly attenuating as shown in FIG. 8A. CFR is a cutoff frequency, and WFR is a total transition frequency width of filter strength (see FIG. 8A). This Mi (ωi) deletes components (high frequency components) from the one-dimensional Fourier space.

Mω (ωi) has the specific of the filter shown in FIG. 8B, which is expressed by the following equation (30):

$$M\omega(\omega i) = |\omega i| \quad (30)$$

FIGS. 8A and 8B show only the characteristics in the plus direction along the horizontal axis. The characteristics in the minus direction along the horizontal axis are omitted since these are in linear symmetry with the characteristics in the plus direction about the vertical axis.

Reverting to FIG. 15, the one-dimensional inverse Fourier transform unit performs a one-dimensional inverse Fourier transform of the image in Fourier space SCF' (i, ω) filtered by |ω| filter function by the |ω| filtering unit to put the image back to real space data and generate a convoluted projection image SC' (i, j).

Figure 16:
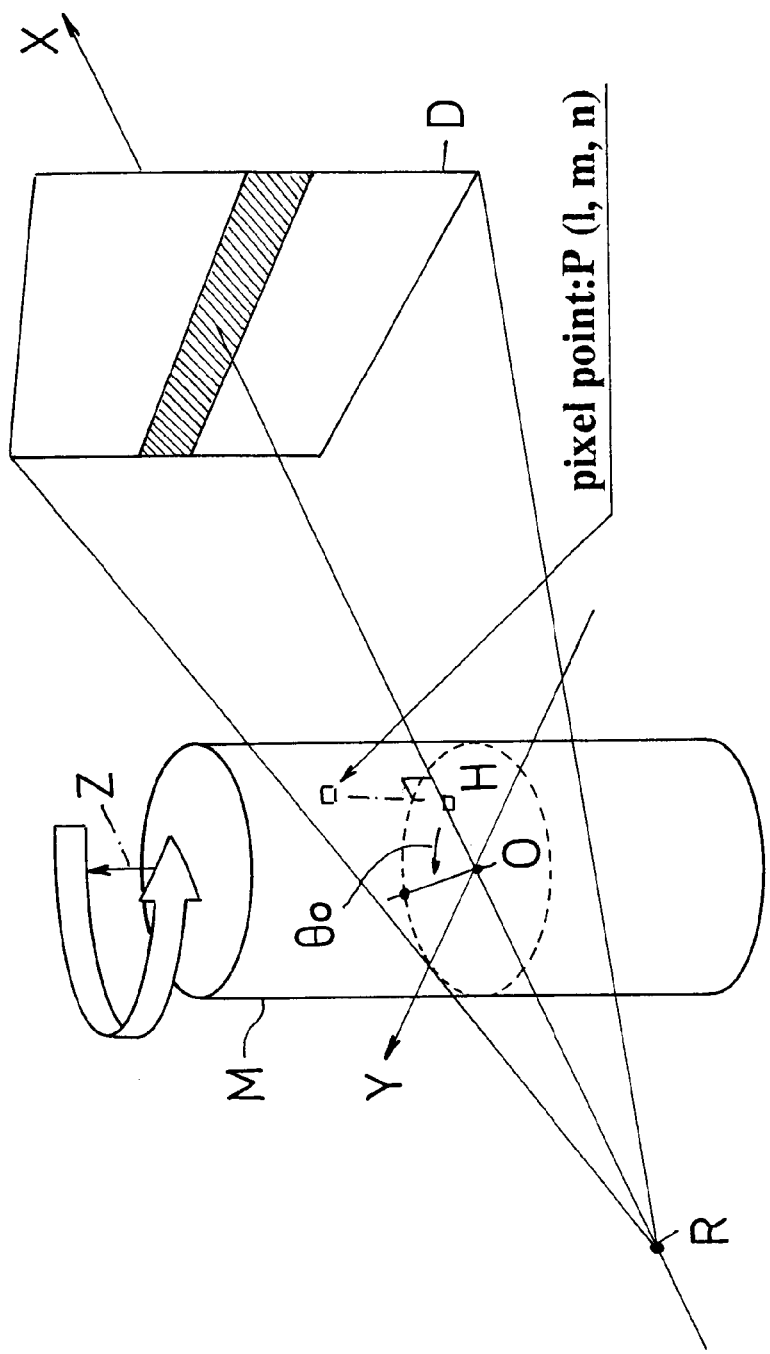
FIG. 16 is a schematic view illustrating convoluted projection data projected back to a virtual three-dimensional lattice.

The second weighting unit 73 performs the second weighting process on the convoluted projection data SC' (i, j) for each scan position, for correcting influences of beam divergence. Specifically, a weight function W (l, m, n) for a three-dimensional pixel point: P (l, m, n) in a coordinate system applied to the patient (see FIG. 16) is derived from the following equation (31):

$$W(l, m, n) = RO^2/(RO + OH)^2 \quad (31)$$

where H is a position on the X-axis of a perpendicular extending from the pixel point P (l, m, n).

Then, as shown in FIG. 9, the second weighting unit 73 determines coordinates (l, J) of the projection image SC' (i,j) of the three-dimensional pixel point: P (l, m, n), and weighting mantissa ($a_z$, $a_y$). The second weighting process is carried out as described above.

Next, the back projection unit 74 performs the predetermined back projection (BP) individually of the projection data after the second weighting process to generate a BP image (three-dimensional volume data). Specifically, an image reconstruction is performed to generate three-dimensional volume data of the region of interest of patient M by projecting the group of projection data of the region of interest detected in the varied scan positions and having undergone the second weighting process, back to predetermined lattice points of a three-dimensional lattice K virtually set to the region of interest as shown in FIG. 9. That is, the simple BP image noted hereinbefore is generated.

Specifically, a back projection based on a computation for linear interpolation is carried out according to the following equation (32):

$$I_n(l, m, n) = I_{n-1}(l, m, n) + W(l, m, n) \times \{W_{11} \cdot SC'(I, J) + W_{12} \cdot SC'(I, J+1) + W_{21} \cdot SC'(I+1, J) + W_{22} \cdot SC'(I+1, J+1)\} \quad (32)$$

where $I_n$ (l, m, n) is an accumulation of back projection, and $I_{n-1}$ (l, m, n) is an accumulation of back projection made by preceding steps.

Pixel spacing of the projection image is standardized to 1, and weight functions in a multiplication weighting method as in the following equations (33)–(36) are used:

$$W_{11} = (1 - a_z) \cdot (1 - a_y) \quad (33)$$

$$W_{12} = (1 - a_z) \cdot a_y \quad (34)$$

$$W_{21} = a_z \cdot (1 - a_y) \quad (35)$$

$$W_{22} = a_z \cdot a_y \quad (36)$$

A similar back projection is performed on the remaining predetermined lattice points of three-dimensional lattice K. Further, a similar back projection is performed for varied scan positions, i.e. over the range of +θmax (+30°) to −θmax (−30°) to generate a BP image (three-dimensional volume data).

The image information storage 52 stores the three-dimensional volume data generated by the back projection unit 74. When the input unit 10 is operated to select image information of any given slice, the image information storage 52 outputs the image information of that slice to the monitor 60.

The monitor 60 has a function to display selected image information stored in the image information storage 52.

In the second embodiment described above, the driver 30 drives the X-ray tube R and flat panel X-ray detector D opposed to each other across the patient M, the X-ray tube R moving on one of the arcuate tracks set on a circumferential track around the patient M to be opposed to each other across the patient M, and the flat panel X-ray detector D synchronously therewith moving on the other arcuate track to maintain a fixed distance from the X-ray tube R, to perform arcuate scanning. The convolution unit 72 performs a convolution process on projection data detected in varied scan positions. The back projection unit 74 projects the projection data convoluted by the convolution unit 72 back to predetermined lattice points of the three-dimensional lattice K virtually set to the region of interest of patient M imaged. In this way, an image reconstruction is carried out to generate three-dimensional volume data of the region of interest. This invention does not use the conventional method in which two-dimensional sectional image data is generated by adding detection signals to superimpose, on a single plane, a plurality of projection images acquired by radiography from varied angles (i.e. projection images acquired from varied scan positions). Instead, an image reconstruction is carried out to generate three-dimensional volume data of the region of interest by projecting projection images acquired from varied scan positions and subjected to the convolution process back to predetermined lattice points of the three-dimensional lattice K. Three-dimensional volume data of the region of interest may be generated without performing radiography a plurality of times. Thus, three-dimensional volume data of the region of interest of patient M is generated quickly.

This invention is not limited to the foregoing embodiments, but may be modified as follows:

(1) In the second embodiment described above, the driver 30 causes the X-ray tube R and flat panel X-ray detector D to move arcuately (for arcuate scanning action). Instead of this arcuate scanning, what is known as linear parallel scanning may be employed in which, as shown in FIG. 17A, the X-ray tube R and flat panel X-ray detector D are opposed to each other across the patient M, the X-ray tube R being movable linearly in a first direction, and the flat panel X-ray detector D being movable synchronously therewith in a second direction counter to the first direction. This linear parallel scanning will be described hereinafter.

In the Feldkamp method which is a cone beam CT reconstruction technique, the line extending from the X-ray tube R through the center axis C falls on the detecting plane of flat panel X-ray detector D perpendicular thereto. An image reconstruction is carried out by applying varied geometric information (conditions such as a distance between X-ray tube R and flat panel X-ray detector D, and a position on the detecting plane where the center axis C appears) as parameters. $I_n$ the arcuate scanning in the second embodiment described above, the X-ray tube R and flat panel X-ray detector D are in the relationship that constantly meets the above requirements. Thus, the image reconstruction is carried out with fixed parameters.

Figure 17B:
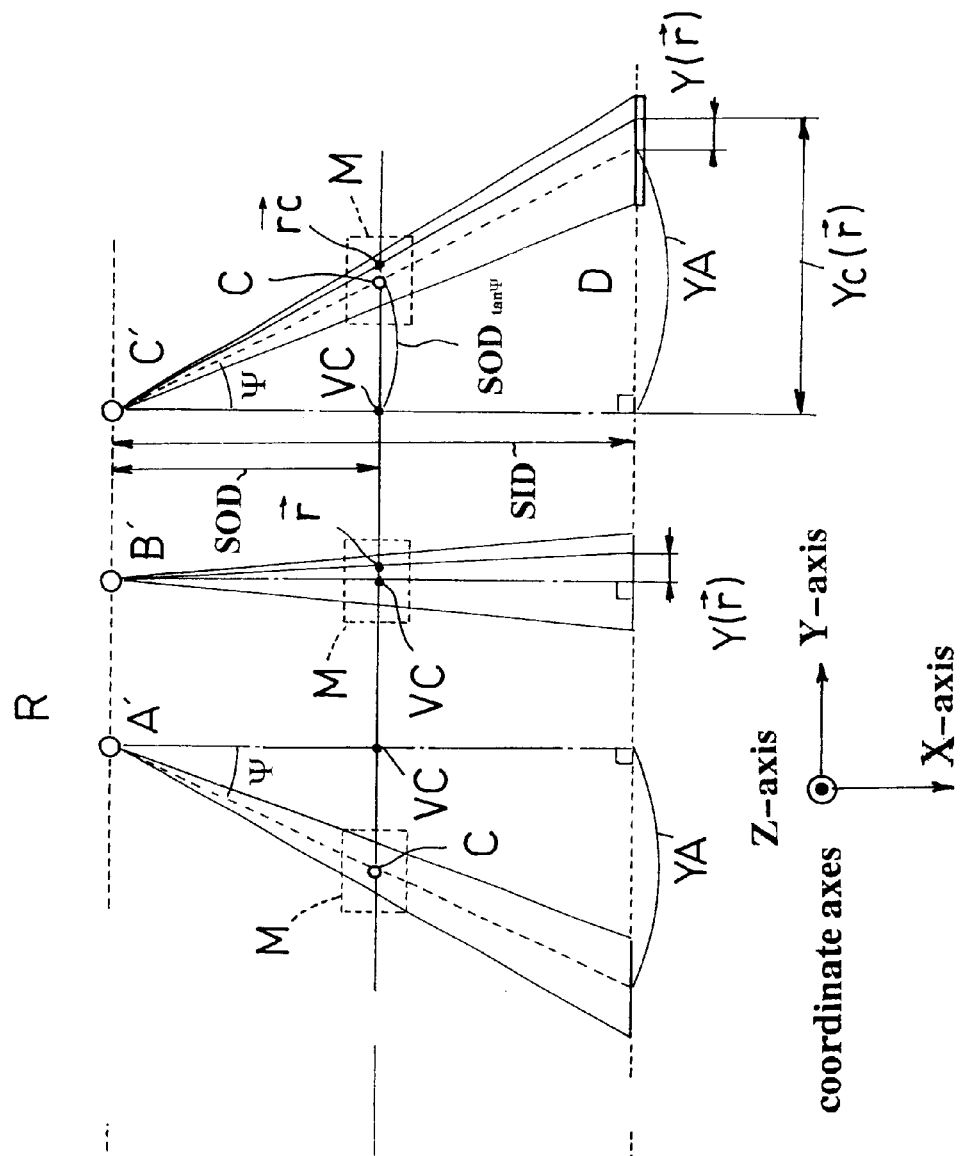
FIGS. 17A and 17B are views illustrating the Feldkamp method used by the non-CT type X-ray radiographic apparatus employing a linear parallel scan mode.
Figure 17A:
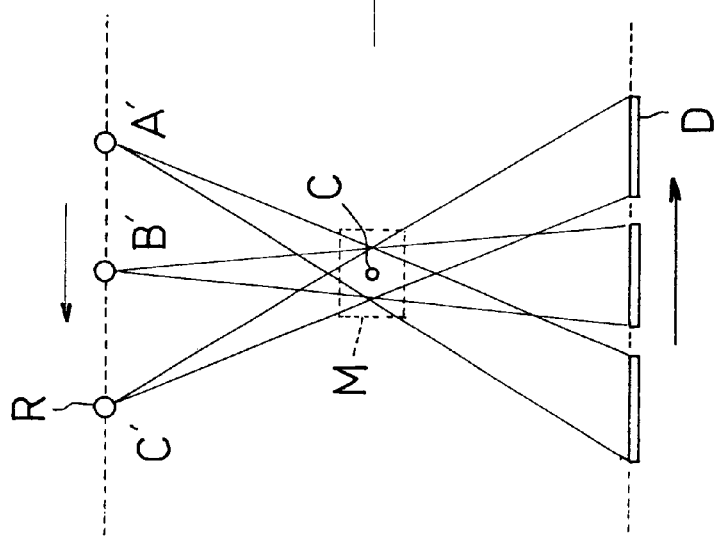

In the linear parallel scanning, however, as shown in FIGS. 17A and 17B, the beam center of X rays emitted in a cone beam from the X-ray tube R toward the patient M is transmitted though the center point O of a particular sectional plane of patient M (a particular point on the center axis C perpendicular to the plane of FIGS. 17A and 17B), but does not constantly impinge on the center point on the detecting plane of flat panel X-ray detector D perpendicular thereto. That is, the incident angle to the center point on the detecting plane of flat panel X-ray detector D is different for each view. It is therefore impossible to use the Feldkamp method directly in such a condition.

Thus, it is assumed that as shown in FIG. 17B, a virtual center axis VC (perpendicular to the plane of FIG. 17B) extends perpendicular to a straight line described by the beam center of X rays emitted in a cone beam from the X-ray tube R toward the patient M and impinging on the center point on the detecting plane of flat panel X-ray detector D perpendicular thereto. The virtual center axis VC extends perpendicular also to the directions of movement of the X-ray tube R and flat panel X-ray detector D, and extends through a sectional plane substantially at the center of the region of interest of patient M. A first perpendicular length SID is assumed for a straight line extending from the X-ray tube R to the center point on the detecting plane of flat panel X-ray detector D. It is further assumed that an angle $\Psi$ is formed between the straight line extending from the X-ray tube R to the center of the detecting plane center of flat panel X-ray detector D, and a sectional axis perpendicular to sectional planes of the region of interest. Then, the length YA of a second perpendicular from the center point on the detecting plane of flat panel X-ray detector D to the straight line, i.e. the first perpendicular, for each view is expressed by YA=SID tan $\Psi$. Thus, the virtual center axis VC is in a different position for each view, though it is parallel to the center axis C and has the same X-axis coordinate as the center axis C. That is, as shown in FIG. 17B, in a position B', the virtual center axis VC coincides with the center axis C, but in positions A' and C', the virtual center axis VC is displaced from the center axis C.

Thus, an image reconstruction may be carried out by varying a parameter (i.e. Y(vr) in equation (21) shown hereinbefore) according to YA=SID·tan $\Psi$, and in accordance with the virtual center axis VC, when a back projection is done for each view. Then, the Feldkamp method may be adopted intact without modifying original image data (e.g. without plane-shifting the original data). As noted in relation to equation (21), the small letter "v" represents vector, and this applies to the description made hereinafter.

The changing of parameter Y(vr) noted above will particularly be described. It is assumed that, as shown in FIG. 17B, the point indicated by vr (called r vector) in position B' and the point indicated by vrc (called rc vector) in position C' are the same point on the three-dimensional lattice K. Regarding the virtual center axis VC as a reference, the relationship between Y-coordinates of the above two points is expressed by the following equation (37):

$$rc_y = r_y + SOD \cdot \tan \Psi \tag{37}$$

where, as shown in position C' of FIG. 17B, SOD is a distance from the X-ray tube R to the virtual center axis VC, $rc_y$ is a distance on the Y-axis from the virtual center axis VC to the point indicated by vrc. As shown in position B' of FIG. 17B, $r_y$ is a distance on the Y-axis from the virtual center axis VC to the point indicated by vr. The center point O of the particular sectional plane of patient M is on the virtual center axis VC.

Assume that X rays emitted from the X-ray tube R through the point vrc are projected to the detecting plane of flat panel X-ray detector D on the point having a Y-coordinate Yc (vr). The actual flat panel X-ray detector D assumes a shift of only YA=SID·tan $\Psi$. Thus, the coordinate on the detecting plane of actual flat panel X-ray detector D is expressed by the following equation (38):

$$Y(vr) = Yc(vr) - SID \cdot \tan \Psi \tag{38}$$

However, Yc (vr)=SID·$rc_y$/SOD.

Thus, an image reconstruction may be carried out only by varying parameter Y (vr) in equation (21) shown hereinbefore (i.e. by coordinate correction), according to the equation (38) above, when a back projection is done for each view. The Feldkamp method may be adopted intact without modifying original image data (e.g. without plane-shifting the original data).

In this way, when the X-ray tube R and flat panel X-ray detector D are moved linearly and parallel to each other, the X-ray tube R and flat panel X-ray detector D may scan the patient M placed in between, to perform non-CT type radiography for an image reconstruction to generate three-dimensional volume data of the region of interest of patient M.

As described above, both of the X-ray tube R and flat panel X-ray detector D are moved arcuately or linearly and parallel to each other. For example, the X-ray tube R may be moved arcuately, with the flat panel X-ray detector D moved linearly. Conversely, the X-ray tube R may be moved linearly, with the flat panel X-ray detector D moved arcuately. In this way, the X-ray tube R and flat panel X-ray detector D may be moved on tracks having different shapes.

Though the X-ray tube R and flat panel X-ray detector D are moved in scanning action, the X-ray tube R may be fixed, with the flat panel X-ray detector D and patient M movable during the scanning, for example. Alternatively, the flat panel X-ray detector D may be fixed, with the X-ray tube R and patient M movable during the scanning. Thus, scanning may be performed by moving any two of the X-ray tube R, flat panel X-ray detector D and patient M.

(2) In the foregoing embodiments, the flat panel X-ray detector D is employed as the area detector. Various other two-dimensional area detectors may be employed, such as an X-ray CCD camera, an image intensifier tube and an imaging plate.

(3) The radiographic apparatus in the foregoing embodiments are used for medical purposes in radiographing patient M. Such radiographic apparatus may be adapted for use in nondestructive testing, for example, of various electronic parts such as BGA (Ball Grid Array) substrates, printed circuit boards and so on.

(4) In the foregoing embodiments, the patient M is irradiated with X rays emitted from the X-ray tube R. Instead of X rays, other penetrating types of electromagnetic waves such as gamma rays and light may be used to produce similar effects. Thus, the radiographic apparatus according to this invention is not limited to X-ray radiographic apparatus. The invention is applicable also to radiographic apparatus for performing radiography by using the types of electromagnetic waves other than X rays that penetrate objects under examination.

The present invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining images of sectional planes in a region of interest of an object under examination by an image reconstruction using projection data acquired by radiographing the object from varied scan positions, said apparatus comprising:
   a radiation source for irradiating said object with penetrating electromagnetic waves;
   an area detector opposed to said radiation source across said object for detecting electromagnetic waves transmitted through said object;
   scanning means for synchronously moving said radiation source and said area detector for scanning action; and
   a back projection unit for performing an image reconstruction to generate three-dimensional volume data of the region of interest by projecting projection data detected in the varied scan positions back to predetermined lattice points of a three-dimensional lattice virtually set to the region of interest of the object radiographed.

2. A radiographic apparatus as defined in claim 1, further comprising a filtering unit for performing an $|\omega|$ filtering process on the projection data detected in the varied scan positions, and outputting the projection data to said back projection unit.

3. A radiographic apparatus as defined in claim 1, wherein said area detector is a flat panel detector or an image intensifier.

4. A radiographic apparatus as defined in claim 1, wherein said scanning means is arranged to move one of said radiation source and said area detector linearly in a first direction, and to move the other linearly in synchronism therewith in a second direction parallel and counter to said first direction.

5. A radiographic apparatus as defined in claim 1, wherein said scanning means is arranged to revolves said radiation source in one of parallel planes opposed to each other across the object, and to revolve said area detector in synchronism therewith in the other parallel plane in a direction counter to a direction of revolution of said radiation source.

6. A radiographic apparatus as defined in claim 1, wherein said scanning means is arranged to set two arcuate tracks on a circumferential track around the object to be opposed to each other across the object, to move said radiation source along one of said arcuate tracks, and to move said area detector in synchronism therewith along the other arcuate track to maintain a fixed distance from said radiation source.

7. A radiographic apparatus as defined in claim 2, wherein said area detector is a flat panel detector or an image intensifier.

8. A radiographic apparatus as defined in claim 2, wherein said scanning means is arranged to move one of said radiation source and said area detector linearly in a first direction, and to move the other linearly in synchronism therewith in a second direction parallel and counter to said first direction.

9. A radiographic apparatus as defined in claim 2, wherein said scanning means is arranged to revolves said radiation source in one of parallel planes opposed to each other across the object, and to revolve said area detector in synchronism therewith in the other parallel plane in a direction counter to a direction of revolution of said radiation source.

10. A radiographic apparatus as defined in claim 2, wherein said scanning means is arranged to set two arcuate tracks on a circumferential track around the object to be opposed to each other across the object, to move said radiation source along one of said arcuate tracks, and to move said area detector in synchronism therewith along the other arcuate track to maintain a fixed distance from said radiation source.

11. A radiographic apparatus as defined in claim 3, wherein said scanning means is arranged to move one of said radiation source and said area detector linearly in a first direction, and to move the other linearly in synchronism therewith in a second direction parallel and counter to said first direction.

12. A radiographic apparatus as defined in claim 3, wherein said scanning means is arranged to revolves said radiation source in one of parallel planes opposed to each other across the object, and to revolve said area detector in synchronism therewith in the other parallel plane in a direction counter to a direction of revolution of said radiation source.

13. A radiographic apparatus as defined in claim 3, wherein said scanning means is arranged to set two arcuate tracks on a circumferential track around the object to be opposed to each other across the object, to move said radiation source along one of said arcuate tracks, and to move said area detector in synchronism therewith along the other arcuate track to maintain a fixed distance from said radiation source.

14. A radiographic apparatus as defined in claim 7, wherein said scanning means is arranged to move one of said radiation source and said area detector linearly in a first direction, and to move the other linearly in synchronism therewith in a second direction parallel and counter to said first direction.

15. A radiographic apparatus as defined in claim 7, wherein said scanning means is arranged to revolves said radiation source in one of parallel planes opposed to each other across the object, and to revolve said area detector in synchronism therewith in the other parallel plane in a direction counter to a direction of revolution of said radiation source.

16. A radiographic apparatus as defined in claim 7, wherein said scanning means is arranged to set two arcuate tracks on a circumferential track around the object to be opposed to each other across the object, to move said radiation source along one of said arcuate tracks, and to move said area detector in synchronism therewith along the other arcuate track to maintain a fixed distance from said radiation source.

17. A radiographic apparatus for obtaining images of sectional planes in a region of interest of an object under examination by an image reconstruction using projection data acquired by radiographing the object from varied scan positions, said apparatus comprising:

a radiation source for irradiating said object with penetrating electromagnetic waves in form of a divergent beam;

an area detector opposed to said radiation source across said object for detecting electromagnetic waves transmitted through said object;

scanning means for setting two non-orbital tracks opposed to each other across the object, moving said radiation source along one of said non-orbital tracks, and moving said area detector in synchronism therewith along the other non-orbital track;

a convolution unit for performing a convolution process on the projection data detected in the varied scan positions; and a back projection unit for performing the image reconstruction to generate three-dimensional volume data of the region of interest by projecting the projection data convoluted by said convolution unit back to predetermined lattice points of a three-dimensional lattice virtually set to the region of interest of the object radiographed.

18. A radiographic apparatus as defined in claim 17, wherein:

said scanning means is arranged to move one of said radiation source and said area detector linearly in a first direction, and to move the other linearly in synchronism therewith in a second direction parallel and counter to said first direction, with the sectional planes to be imaged of the object placed in between; and said back projection unit is arranged to project the projection data for the varied scan positions back to the predetermined lattice points of the three-dimensional lattice, coordinates of said projection data being corrected according to an angle formed between a virtual center axis of revolution extending substantially through the center of the region of interest of the object and perpendicular to the sectional planes to be imaged, and a straight line extending from said radiation source in each of said varied scan positions to the center of said area detector.

19. A radiographic apparatus as defined in claim 17, wherein said area detector is a flat panel detector or an image intensifier.

20. A radiographic apparatus as defined in claim 18, wherein said area detector is a flat panel detector or an image intensifier.

* * * * *